United States Patent [19]

Petrzilka et al.

[11] Patent Number: 4,709,030
[45] Date of Patent: Nov. 24, 1987

[54] NOVEL LIQUID CRYSTAL MIXTURES

[75] Inventors: Martin Petrzilka, Kaiseraugst; Martin Schadt, Seltisberg, both of Switzerland

[73] Assignee: Hoffmann-La Roche Inc., Nutley, N.J.

[21] Appl. No.: 884,571

[22] Filed: Jul. 11, 1986

Related U.S. Application Data

[62] Division of Ser. No. 749,163, Jun. 26, 1985, Pat. No. 4,621,901.

[30] Foreign Application Priority Data

Jul. 12, 1984 [CH] Switzerland ............ 3385/84
May 6, 1985 [CH] Switzerland ............ 1899/85

[51] Int. Cl.$^4$ ............ C09K 3/34; C09K 19/42; C07C 13/28; C07C 15/12; C07C 25/18; G02F 1/13

[52] U.S. Cl. ............ 544/242; 252/299.5; 252/299.6; 252/299.61; 252/299.63; 252/299.65; 252/299.66; 252/299.67; 350/350 R; 350/350 S; 544/298; 544/315; 544/316; 544/318; 544/335; 549/369; 549/372; 549/373; 549/374; 549/375; 558/17; 558/414; 558/415; 558/416; 558/426; 558/430; 558/431; 560/1; 560/55; 560/59; 560/64; 560/65; 560/73

[58] Field of Search ............ 252/299.6, 299.5, 299.61, 252/299.63, 299.65, 299.66, 299.67; 350/350 R, 350 S; 570/128, 129, 130; 585/20, 25; 544/315, 316, 318, 335, 298, 242; 549/369, 372, 373, 374, 375; 558/17, 414, 415, 416, 426, 430, 431; 560/59, 64, 65, 73, 55, 102, 104, 106, 107, 108, 109, 116, 118, 51, 126, 128; 568/329, 331, 367, 425, 420, 642, 647, 631, 659, 661, 664

[56] References Cited

U.S. PATENT DOCUMENTS

| | | | |
|---|---|---|---|
| 3,819,531 | 6/1974 | Saeva et al. | 252/299.63 |
| 3,947,375 | 3/1976 | Gray et al. | 252/299.66 |
| 4,147,655 | 4/1979 | Dubois et al. | 252/299.67 |
| 4,211,666 | 7/1980 | Inukai et al. | 252/299.66 |
| 4,358,391 | 11/1982 | Finkelmann et al. | 252/299.61 |
| 4,363,767 | 12/1982 | Demus et al. | 252/299.63 |
| 4,460,770 | 7/1984 | Petrzilka et al. | 252/299.63 |
| 4,505,837 | 3/1985 | Romer et al. | 252/299.5 |
| 4,528,114 | 7/1985 | Petrzilka et al. | 252/299.63 |
| 4,550,981 | 11/1985 | Petrzilka et al. | 252/299.63 |
| 4,565,425 | 1/1986 | Petrzilka et al. | 252/299.63 |
| 4,605,520 | 8/1986 | Bezborodov et al. | 252/299.65 |
| 4,621,901 | 11/1986 | Petrzilka et al. | 252/299.63 |
| 4,630,896 | 12/1986 | Petrzilka et al. | 252/299.63 |
| 4,654,421 | 3/1987 | Tamaka et al. | 252/299.63 |

FOREIGN PATENT DOCUMENTS

| | | | |
|---|---|---|---|
| 56501 | 7/1982 | European Pat. Off. | 252/299.63 |
| 122389 | 10/1984 | European Pat. Off. | 252/299.63 |
| 168683 | 1/1986 | European Pat. Off. | 252/299.63 |
| 169327 | 1/1986 | European Pat. Off. | 252/299.63 |
| 3510434 | 9/1986 | Fed. Rep. of Germany | 252/299.63 |
| 3510432 | 9/1986 | Fed. Rep. of Germany | 252/299.63 |
| 52-13484 | 2/1977 | Japan | 252/299.63 |
| 57-67538 | 4/1982 | Japan | 252/299.63 |
| 57-70851 | 5/1982 | Japan | 252/299.64 |
| 59-199649 | 11/1984 | Japan | 252/299.66 |
| 60-112723 | 6/1985 | Japan | 252/299.63 |
| 61-27929 | 2/1986 | Japan | 252/299.63 |
| 61-27928 | 2/1986 | Japan | 252/299.63 |
| 61-27931 | 2/1986 | Japan | 252/299.66 |
| 85/01295 | 3/1985 | World Int. Prop. O. | 252/299.63 |
| 1432692 | 4/1976 | United Kingdom | 252/299.64 |
| 2002767 | 2/1979 | United Kingdom | 252/299.01 |
| 2078727 | 1/1982 | United Kingdom | 252/299.6 |

OTHER PUBLICATIONS

Petrzilka, M., Abstract of the 13th Frieburger Arbeitstagunl Flussigkristalle, Freiburg, Germany (Mar. 23–25, 1983).
Dabrowski, R. et al., Mol. Cryst. Liq. Cryst., vol. 87, pp. 109–135, (1982).
Petrzilka, M., Mol. Cryst. Liq. Cryst., vol. 111, pp. 324–358, (Nov. 1984).
Goodby, J. W. et al., Liq. Cryst. Ordered Fluids, vol. 4, pp. 89–110, (1984).
Kamogawa, H. et al., Bull. Chem. Soc. JPN, vol. 56, pp. 3517–3518, (Nov. 1983).
Finkelman, H., Phil. Trans. R. Soc. Lond. A, vol. 309, pp. 105–114, (1983).

Primary Examiner—Teddy S. Gron
Attorney, Agent, or Firm—Jon S. Saxe; Bernard S. Leon; George W. Johnston

[57] ABSTRACT

Liquid crystalline mixtures containing compounds of the formula

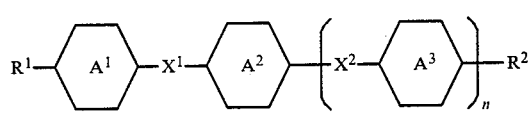

wherein n stands for the number 0 or 1; $X^1$ and $X^2$ denote single covalent bonds or one of the symbols $X^1$ and $X^2$ also denotes —COO—, —OOC— or —CH$_2$CH$_2$—; the rings $A^1$, $A^2$ and $A^3$ represent 1,4-phenylene, 2-fluoro-1,4-phenylene or trans-1,4-cyclohexylene or one of these rings also represents a 2,5-disubstituted pyrimidine ring or a trans-2,5-disubstituted m-dioxane ring; $R^1$ signifies 4-alkenyl or on a cyclohexyl ring also 2Z-alkenyl; and $R^2$ denotes alkyl, alkoxy, —CN or —NCS, as well as the manufacture of these compounds and the use for electro-optical purposes are described.

10 Claims, No Drawings

NOVEL LIQUID CRYSTAL MIXTURES

This is a division of application Ser. No. 749,163 filed June 26, 1985, now U.S. Pat. No. 4,621,901.

BACKGROUND OF THE INVENTION

1. Field of the Invention

This invention relates to liquid crystalline compounds and mixtures.

2. Description

Liquid crystals have recently gained considerable importance as dielectrics in indicating devices, since the optical properties of such substances can be influenced by an applied voltage. Electro-optical devices based on liquid crystals are well known to the person skilled in the art and can be based on various effects such as, for example, the dynamic scattering, the deformation of aligned phases (DAP cell) the Schadt-Helfrich effect (twisted-nematic cell), the guest/host effect (guest/host cell) or a cholesteric-nematic phase transition (phase change cell).

The liquid crystals which are used must have a good stability towards heat, moisture, air, electromagnetic radiation, electrical fields and the like. Further, they should be colourless, should have short response times and low viscosity and should give a good contrast. Since liquid crystals are usually used as mixtures, it is, moreover, important that the components have a good miscibility with one another and at the same time form a nematic or cholesteric mesophase. Other properties such as, for example, the electrical conductivity, the threshold potential, the multiplexibility and the dielectric anisotropy must fulfil different conditions depending on the type of cell which is used.

SUMMARY

The present invention is concerned with novel liquid crystalline mixtures which contain components having a 4-alkenyl or a 2Z-alkenyl side-chain and with the use of these compounds and mixtures for electro-optical purposes. The invention is also concerned with the novel 4-alkenyl and 2Z-alkenyl compounds and with their manufacture.

DETAILED DESCRIPTION OF THE INVENTION

The present invention concerns liquid crystalline mixtures containing one or more compounds of the formula

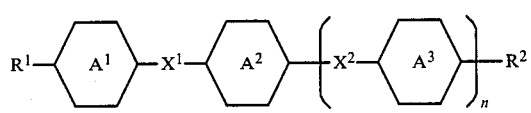

wherein n stands for the integer 0 or 1; $X^1$ and $X^2$ are single covalent bonds or one of the symbols $X^1$ and $X^2$ also is —COO—, —OOC— or —CH$_2$CH$_2$—; the rings $A^1$, $A^2$ and $A^3$ independently are 1,4-phenylene, 2-fluoro-1,4-phenylene or trans-1,4-cyclohexylene or one of these rings also is 2,5-disubstituted pyrimidine or trans-2,5-disubstituted m-dioxane; $R^1$ is 4-alkenyl or when positioned on a cyclohexyl ring $R^1$ also can be 2Z-alkenyl; and $R^2$ is alkyl, alkoxy, —CN or —NCS.

The term "4-alkenyl" signifies in the scope of the present invention unsaturated, univalent aliphatic residues such as 4-pentenyl and the E- and/or Z-form of 4-hexenyl, 4-heptenyl, 4-octenyl, 4-nonenyl, 4-decenyl, 4-undecenyl and 4-dodecenyl. The term "2Z-alkenyl" embraces unsaturated, univalent aliphatic residues such as allyl, 2Z-butenyl, 2Z-pentenyl, 2Z-hexenyl, 2Z-heptenyl, 2Z-octenyl, 2Z-nonenyl, 2Z-decenyl, 2Z-undecenyl and 2Z-dodecenyl. The term "alkyl" embraces straight-chain and branched chain alkyl residues of 1 to 12 carbon atoms such as methyl, ethyl, propyl, isopropyl, butyl, 2-methylbutyl, pentyl, hexyl, heptyl, octyl, nonyl, decyl, undecyl and dodecyl. The term "alkoxy" embraces alkyloxy residues in which the alkyl portion has the above significance. The term "halogen" signifies in the scope of the present invention chlorine, bromine or iodine. The term "alkali metal" embraces lithium, sodium and potassium.

It has been found that the compounds of formula I and their mixtures have the requisite properties mentioned earlier and, moreover, have low viscosities, especially an improved rotation viscosity $\gamma_1$ and make possible comparatively low threshold potentials. Further, the compounds of formula I have a favourable ratio of the elastic constants $k_{33}$ (bend) and $k_{11}$ (splay) and therefore give steep transmission curves and a good multi-plexibility.

The compounds of formula I and their mixtures can be used in principle in any electro-optical devices. However, they are preferably used in twisted-nematic cells and in guest/host cells.

The manufacture of the mixtures in accordance with the invention and of the electro-optical devices can be carried out in a manner known per se.

The mixtures in accordance with the invention conveniently contain a liquid crystalline carrier material and one or more compounds of formula I. The amount of compounds of formula I can vary in relatively wide limits. In general, the mixtures in accordance with the invention contain at least about 1 wt.% of compounds of formula I. The amount of compounds of formula I preferably amounts to about 5–50 wt.%.

The mixtures in accordance with the invention can contain, in addition to one or more compounds of formula I, usual liquid crystal components such as e.g. substances from the classes of Schiff's bases, azobenzenes, azoxybenzenes, phenylbenzoates, cyclohexanecarboxylic acid phenyl esters, cyclohexanecarboxylic acid cyclohexyl esters, biphenyls, terphenyls, phenylcyclohexanes, cyclohexylbiphenyls, phenylpyrimidines, diphenylpyrmidines, cyclohexylphenylpyrimidines, phenyldioxanes, 2-cyclohexyl-1-phenylethanes and the like. Such substances are known to the person skilled in the art and many of them are, moreover, commercially obtainable.

The mixtures in accordance with the invention preferably contain, besides the compounds of formula I, one or more compounds of the general formulae

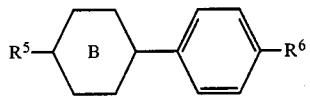   VIII

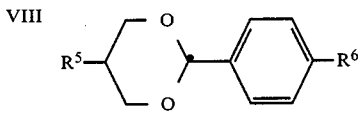   IX

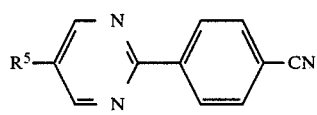 X

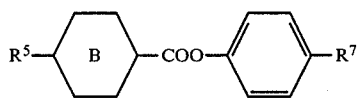 XI

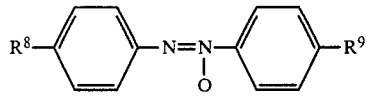 XII

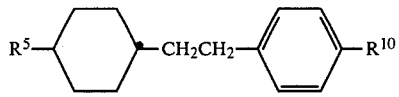 XIII

 XIV

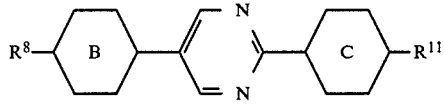 XV

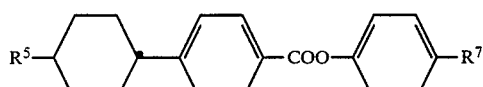 XVI

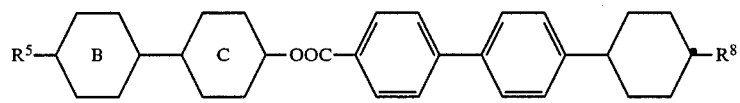

XVII

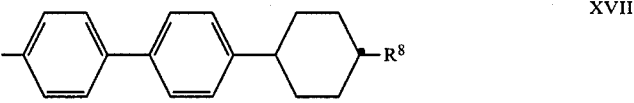

wherein the rings B and C represent 1,4-phenylene or trans-1,4-cyclohexylene; $R^5$ signifies straight-chain $C_1$–$C_7$-alkyl, straight-chain $C_4$–$C_7$-3E-alkenyl or a cyclohexane or dioxane ring also $C_2$–$C_7$-1E-alkenyl; $R^6$ signifies straight-chain $C_1$–$C_7$-alkyl, straight-chain $C_1$–$C_7$-alkoxy, —CN or —NCS; $R^7$ denotes straight-chain $C_1$–$C_7$-alkyl or straight-chain $C_1$–$C_7$-alkoxy; $R^8$ and $R^9$ stand for straight-chain $C_1$–$C_7$-alkyl; $R^{10}$ represents cyano, alkyl, alkoxy, p-alkylphenyl, p-alkoxypenyl, trans-4-alkylcyclohexyl, 4'-alkyl-4-biphenylyl, p-(trans-4-alkylcyclohexyl)phenyl, 2-(trans-4-alkylcyclohexyl)ethyl, p-[2-(trans-4-alkylcyclohexyl)ethyl]-phenyl or 2-[p-(trans-4-alkylcyclohexyl)phenyl]ethyl, and the alkyl and alkoxy residues in $R^{10}$ are straight-chain residues with 1 to 7 carbon atoms; and $R^{11}$ signifies cyano or straight-chain $C_1$–$C_7$-alkyl.

The mixtures in accordance with the invention can also contain optically active compounds (e.g. optically active biphenyls) and/or dichroic colouring substances (e.g. azo, azoxy or anthraquinone colouring substances). The amount of such substances is determined by the solubility, the desired pitch, colour, extinction and the like. Preferably, the amount of optically active compounds amounts to a maximum of about 4 wt.% and the amount of dichroic colouring substances amounts to a maximum of about 10 wt.% in the total mixture.

The compounds of formula I in which simultaneously $R^1$ does not signify 4-pentenyl, ring $A^1$ does not signify trans-1,4-cyclohexylene, $X^1$ does not signify —CH$_2$CH$_2$—, ring $A^2$ does not signify 1,4-phenylene, n does not signify the number O and $R^2$ does not signify —CN are novel and are also an object of the present invention.

Formula I above embraces, in particular, the following formulae:

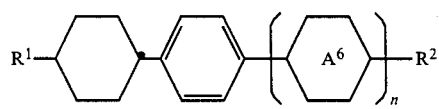 Ia

-continued

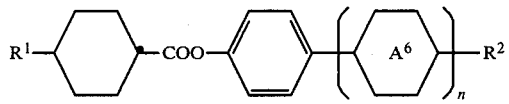 Ib

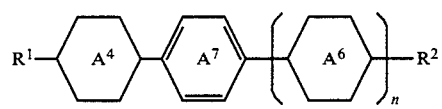 Ic

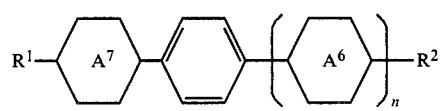 Id

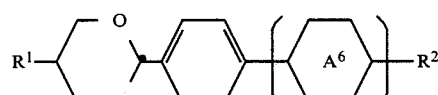 Ie wherein $R^1$, $R^2$ and n have the above significances; the rings $A^4$ and $A^6$ represent 1,4-phenylene, 2-fluoro-1,4-phenylene or trans-1,4-cyclohexylene; and ring $A^7$ denotes a 2,5-disubstituted pyrimidine ring.

In general there are preferred those compounds of formula I in which $X^1$ and $X^2$ denote single covalent bonds or one of these symbols also denotes —COO— or —OOC—. Further, there are in general preferred those compounds of formula I in which $R^1$ signifies 4-alkenyl, especially 4Z-alkenyl. Preferably, $R^1$ stands for straight-chain residues with up to 12 carbon atoms, i.e. for straight-chain 2Z-alkenyl with 3 to 12 carbon atoms or especially for straight-chain 4-alkenyl with 5 to 12 carbon atoms such as 4-pentenyl, 4Z-hexenyl, 4E-hexenyl, 4Z-heptenyl and 4E-heptenyl.

$R^2$ preferably signifies —CN, —NCS or a straight-chain alkyl or alkoxy group with 1 to 12, especially 1 to 7, carbon atoms. The residues —CN, —NCS and alkoxy for R² are preferably present on an aromatic ring, i.e. on a benzene or pyrimidine ring.

A lateral fluorine substituent which is optionally present in formula I is preferably situated in the ortho-position to R², especially when R² denotes —CN or —NCS. In general, however, there are preferred those compounds of formula I which have no lateral fluorine substituents.

Especially preferred compounds of formulae I, Ia, Ib, Ic, Id and Ie are therefore those in which n stands for the number 0 or 1; X¹ and X² denote single covalent bonds or one of the symbols X¹ and X² also denotes —COO— or —OOC—; the rings A¹, A², A³, A⁴ and A⁶ represent 1,4-phenylene or trans-1,4-cyclohexylene or one of the rings A¹, A² and A³ also represents a 2,5-disubstituted m-dioxane ring; ring A⁷ denotes a 2,5-disubstituted pyrimidine ring; R¹ signifies straight-chain 4-alkenyl with 5 to 12 carbon atoms; and R² denotes straight-chain C₁-C₁₂-alkyl or on a benzene or pyrimidine ring also —CN, —NCS or straight-chain C₁-C₁₂-alkoxy.

Examples of preferred compounds of formula I are:
p-[trans-4-(4-Pentenyl)cyclohexyl]benzonitrile,
p-[trans-4-(4-pentenyl)cyclohexyl]phenyl isothiocyanate,
p-[trans-4-(4Z-hexenyl)cyclohexyl]benzonitrile,
p-[trans-4-(4Z-hexenyl)cyclohexyl]phenyl isothiocyanate,
1-ethyl-4-[trans-4-(4-pentenyl)cyclohexyl]benzene,
1-ethyl-4-(trans-4-allylcyclohexyl)benzene,
1-ethoxy-4-[trans-4-(4-pentenyl)cyclohexyl]benzene,
1-ethoxy-4-(trans-4-allylcyclohexyl)benzene,
1-ethyl-b 4-[2-(trans-4-(4-pentenyl)cyclohexyl)ethyl]benzene,
1-ethyl-4-[2-(trans-4-allylcyclohexyl)ethyl]benzene,
4'-(4-pentenyl)-4-biphenylcarbonitrile,
4'-[trans-4-(4-pentenyl)cyclohexyl]-4-biphenylcarbonitrile,
trans-4-(4-pentenyl)cyclohexanecarboxylic acid p-ethoxyphenyl ester,
p-[trans-4-(4-pentenyl)cyclohexyl]benzoic acid p-propylphenyl ester,
5-[p-(4-pentenyl)phenyl]-2-pyrimidinecarbonitrile,
5-[p-(4-pentenyl)phenyl]-2-pyrimidinyl isothiocyanate,
p-[5-(4-pentenyl)-2-pyrimidinyl]benzonitrile,
p-[5-(4-pentenyl)-2-pyrimidinyl]phenyl isothiocyanate,
p-[trans-5-(4-pentenyl)-m-dioxan-2-yl]benzonitrile,
p-[trans-5-(4-pentenyl)-m-dioxan-2-yl]phenyl isothiocyante
and the compounds of formula I named in the chemical Examples hereinafter.

The compounds of formula I can be manufactured in accordance with the invention by the following process:

(a) for the manufacture of the compounds of formula I in which X¹ or X² denotes —COO— or —OOC—, esterifying a compound of the formula

or a reactive derivative thereof with a compound of the formula

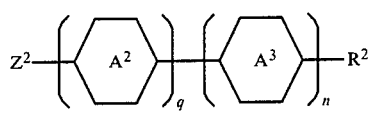

wherein one of the groups Z¹ and Z² represents —COOH and the other represents —OH; one of the indices p and q denotes the number 0 and the other denotes the number 1; and R¹, R², n and the rings A¹, A² and A³ have the above significance, or a reactive derivative thereof, or (b) for the manufacture of the compounds of formula I in which one of the rings A¹, A² and A³ represents a trans-2,5-disubstituted m-dioxane ring and X¹ and X² denote single covalent bonds or one of these symbols also denotes —CH₂CH₂—, reacting a compound of the general formula

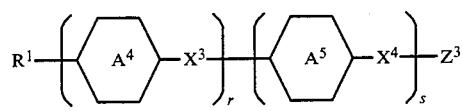

with a compound of the formula

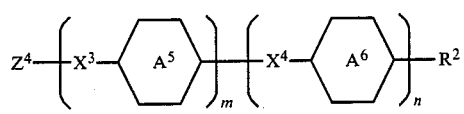

wherein one of the groups Z³ and Z⁴ represents —CH(CH₂OH)₂ and the other represents —CHO; X³ and X⁴ denote single covalent bonds or one of these symbols also denotes —CH₂CH₂—; the rings A⁴, A⁵ and A⁶ represent 1,4-phenylene, 2-fluoro-1,4-phenylene or trans-1,4-cyclohexylene; m, n, r and s signify the numbers 0 or 1 and the sum (m+n+r+s) of these indices is 1 or 2, whereby s can only signify the number 1 when r stands for the number 1 and m can only signify the number 1 when r stands for the number 0; and R¹ and R² have the above significances, or (c) for the manufacture of the compounds of formula I in which one of the rings A¹, A² and A³ represents a 2,5-disubstituted pyrimidine ring and X¹ and X² denote single covalent bonds or one of these symbols also denotes —CH₂CH₂—, reacting a compound of general formula IV with a compound of formula V in which one of the groups Z³ and Z⁴ represents

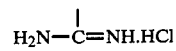

and the other represents

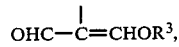

R³ denotes alkyl and X³, X⁴, R¹, R², m, n, r, s and the rings A⁴, A⁵ and A⁶ have the above significances, in the presence of a base, or (d) for the manufacture of the compounds of formula I in which $X^1$ and $X^2$ denote single covalent bonds or one of these symbols also denotes —CH$_2$CH$_2$—, reacting a compound of the formula

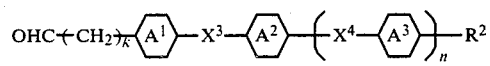
VI wherein $X^3$ and $X^4$ denote single covalent bonds or one of these symbols also denotes —CH$_2$CH$_2$—; $R^2$, n and the rings $A^1$, $A^2$ and $A^3$ have the above significances; and k represents the number 3 or, when ring $A^1$ represents trans-1,4-cyclohexylene, also the number 1, with an alkyltriphenylphosphonium halide in the presence of a base, or (e) for the manufacture of the compounds of formula I in which $R^2$ denotes —NCS, reacting a compound of the formula

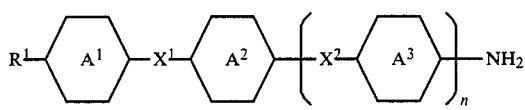
VII wherein $R^1$, $X^1$, $X^2$, n and the rings $A^1$, $A^2$ and $A^3$ have the above significances, with thiophosgene in the presence of an amine, or (f) for the manufacture of the compounds of formula I in which $X^1$ and $X^2$ denote single covalent bonds or one of these symbols also denotes —CH$_2$CH$_2$—, the rings $A^1$, $A^2$ and $A^3$ represent 1,4-phenylene, 2-fluoro-1,4-phenylene or trans-1,4-cyclohexylene and $R^2$ signifies primary alkyl, reducing a compound of the formula

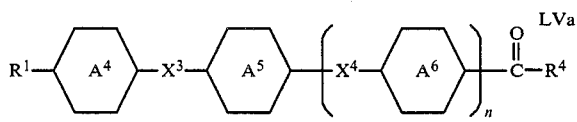
LVa wherein $X^3$ and $X^4$ denote single covalent bonds or one of these symbols also denotes —CH$_2$—CH$_2$—; the rings $A^4$, $A^5$ and $A^6$ represent 1,4-phenylene, 2-fluoro-1,4-phenylene or trans-1,4-cyclohexylene; $R^4$ signifies hydrogen or alkyl; and $R^1$ and n have the above significances.

The esterification of the compounds of formulae II and III or of reactive derivatives thereof (e.g. acid chloride, alkali metal alcoholate or alkali metal phenolate) in accordance with process variant (a) can be carried out in a manner known per se. The esterification of the acid chlorides can be carried out, for example, in diethyl ether, tetrahydrofuran, dimethylformamide, benzene, toluene, carbon tetrachloride, pyridine and the like. The esterification of a compound of formula II with a compound of formula III is preferably carried out in the presence of 4-(dimethylamino)pyridine and dicyclohexylcarbodiimide or in the presence of oxalyl chloride and dimethylformamide. The temperature and pressure at which these esterification reactions are carried out are not critical. In general, these reactions are carried out at atmospheric pressure and a temperature between about −30° C. and the boiling temperature of the reaction mixture.

The reaction of a compound of formula IV with a compound of formula V in accordance with process variant (b) can be carried out in a manner known per se. In place of the aldehyde there can also be used a suitable acetal, e.g. the dimethyl acetal. The reaction is conveniently carried out in an inert organic solvent (for example, an aromatic hydrocarbon such as benzene, toluene or xylene) in the presence of a catalytic amount of an organic or inorganic acid such as p-toluenesulphonic acid or dry hydrochloric acid. The temperature and pressure are not critical, but the reaction is preferably carried out at reflux temperature and atmospheric pressure.

The reaction of a compound of formula IV with a compound of formula V in accordance with process variant (c) can also be carried out in a manner known per se. The reaction is conveniently carried out in water or an organic solvent (preferably an alcohol such as methanol, ethanol, ethylene glycol and the like) in the presence of a base, preferably an alkali metal alcoholate such as sodium methylate or sodium ethylate. $R^3$ conveniently embraces alkyl residues with 1 to 5 carbon atoms such as methyl, ethyl, propyl, isopropyl and the like. The temperature and pressure at which this reaction is carried out are not critical. However, in general, the reaction is carried out at atmospheric pressure and a temperature between room temperature and the reflux temperature.

The reaction of a compound of formula VI with an alkyl-triphenylphosphonium halide (preferably an alkyltriphenylphosphonium bromide) in the presence of a base (in accordance with process variant (d) can be carried out in a manner known per se. Suitable bases are potassium t-butylate, sodium methylate, potassium carbonate, sodium hydride, sodium amide and the like. The reaction is conveniently carried out in an inert organic solvent, for example an ether such as diethyl ether, tetrahydrofuran or dioxan. The temperature and pressure are not critical; in general, however, the reaction is carried out at atmospheric pressure and a temperature of room temperature up to the reflux temperature.

The reaction of a compound of formula VII with thiophosgene in the presence of an amine in accordance with process variant (e) can be carried out in a manner known per se. The reaction is conveniently carried out in an inert organic solvent, for example a chlorinated or aromatic hydrocarbon or an ether such as chloroform, methylene chloride, benzene, diethyl ether, tetrahydrofuran and the like. Preferred bases are dialkylamines and especially trialkylamines such as diisopropylamine, triethylamine and the like. The temperature and pressure are not critical. In general, however, the reaction is carried out at atmospheric pressure and a temperature of −30° C. to the reflux temperature, preferably at room temperature.

The reduction of a compound of formula LVa in accordance with process variant (f) can be carried out in a manner known per se. For example, a compound of formula LVa can be reacted with hydrazine in the presence of a base (e.g. potassium hydroxide, sodium ethylate, potassium t-butylate) in an inert organic solvent such as dimethylformamide, ethanol, diethylene glycol or triethylene glycol and subsequently the hydrazone formed can be decomposed at elevated temperature. A preferred variant is the reaction according to the Huang-Minlon process, i.e. heating the compound of formula LVa under reflux in a high-boiling solvent which is miscible with water (e.g. diethylene glycol or triethylene glycol) together with hydrazine hydrate and potassium hydroxide, subsequently distilling off the water until the hydrazone has decomposed and boiling the mixture under reflux until the reduction has finished. Further, the compounds of formula LVa can be reduced by heating with amalgamated zinc and hydrochloric acid; if desired, an organic solvent such as ethanol, acetic acid, dioxan or toluene can be added to the reaction mixture.

The compounds of formulae III and V above are known or are analogues of known compounds.

The compounds of formula LVa are novel and are also an object of the present invention. They can be obtained in a manner known per se from the corresponding compounds of formula I in which $R^2$ signifies cyano. For example, the compounds of formula LVa in which $R^4$ signifies hydrogen are obtained by reducing the cyano compounds with diisobutylaluminium hydride and the compounds of formula LVa in which $R^4$ signifies alkyl are obtained by reacting the cyano compounds with an alkylmagnesium halide and subsequently hydrolyzing the reaction product.

The compounds of formulae II, IV, VI and VII are also novel. The preparation of these compounds and further alternatives for the manufacture of the compounds of formula I are illustrated on the basis of representative examples in the following Reaction Schemes 1–8 in which $R^1$ and $R^2$ have the above significances, ring $A^5$ represents 1,4-phenylene, 2-fluoro-1,4-phenylene or trans-1,4-cyclohexylene, R and $R^4$ denotes hydrogen or alkyl and Ts stands for p-tosyl.

Scheme 1

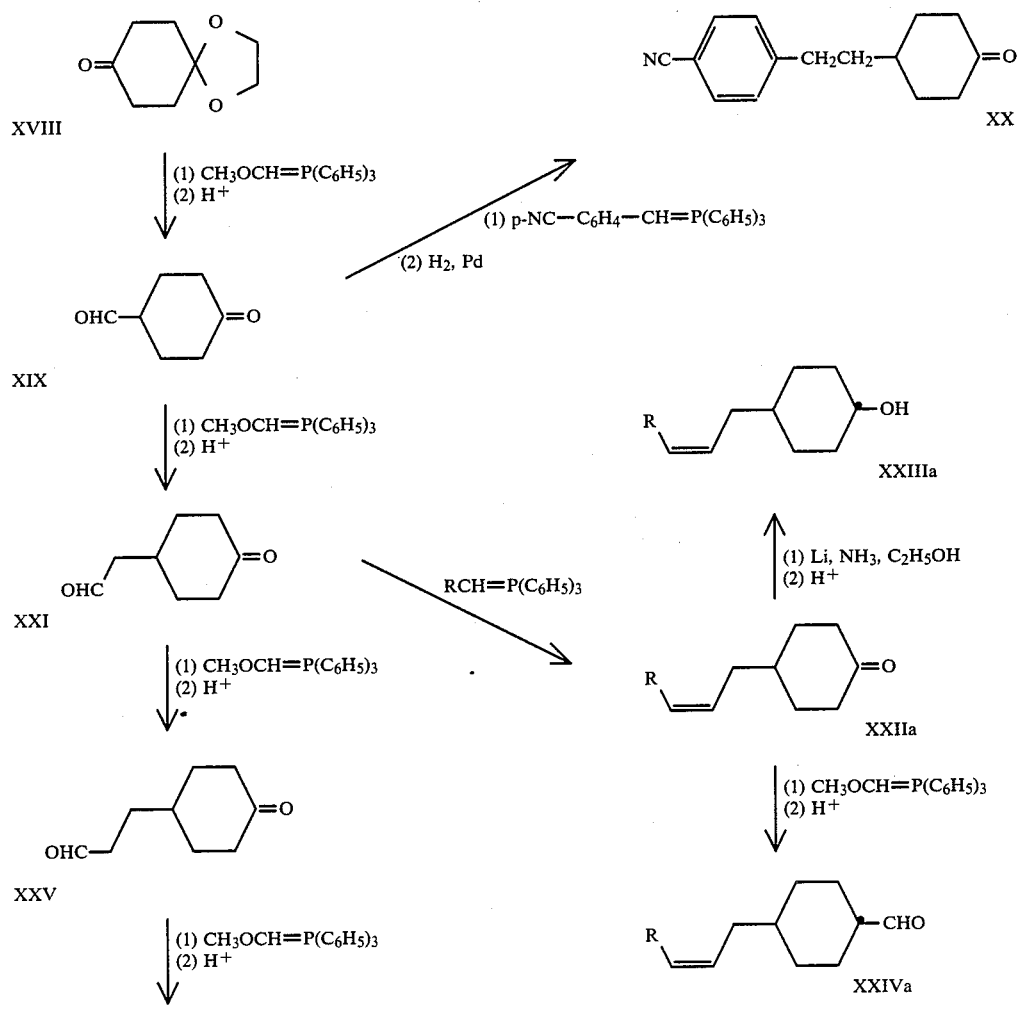

Scheme 1
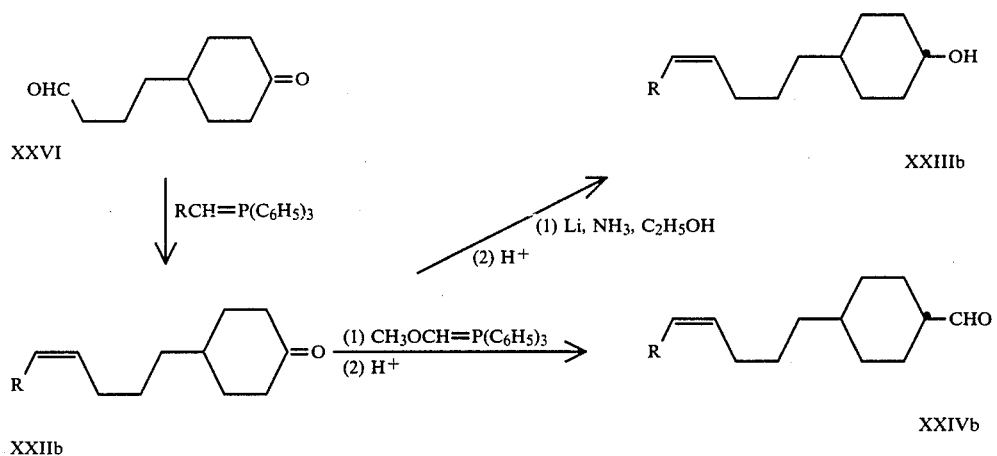
Scheme 2
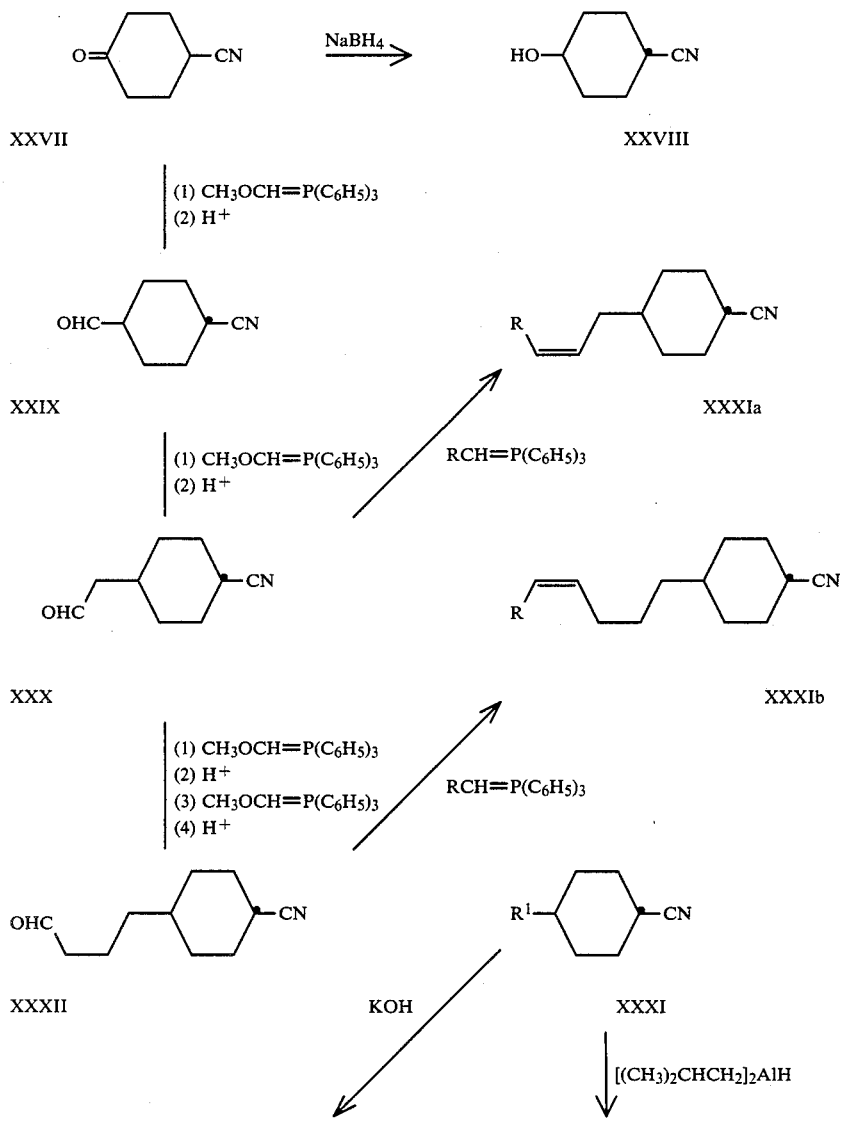

Scheme 2
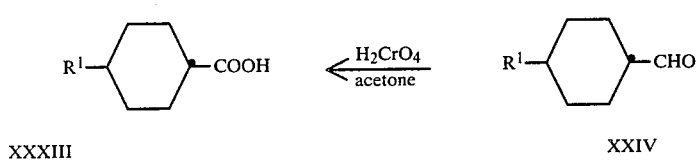
Scheme 3
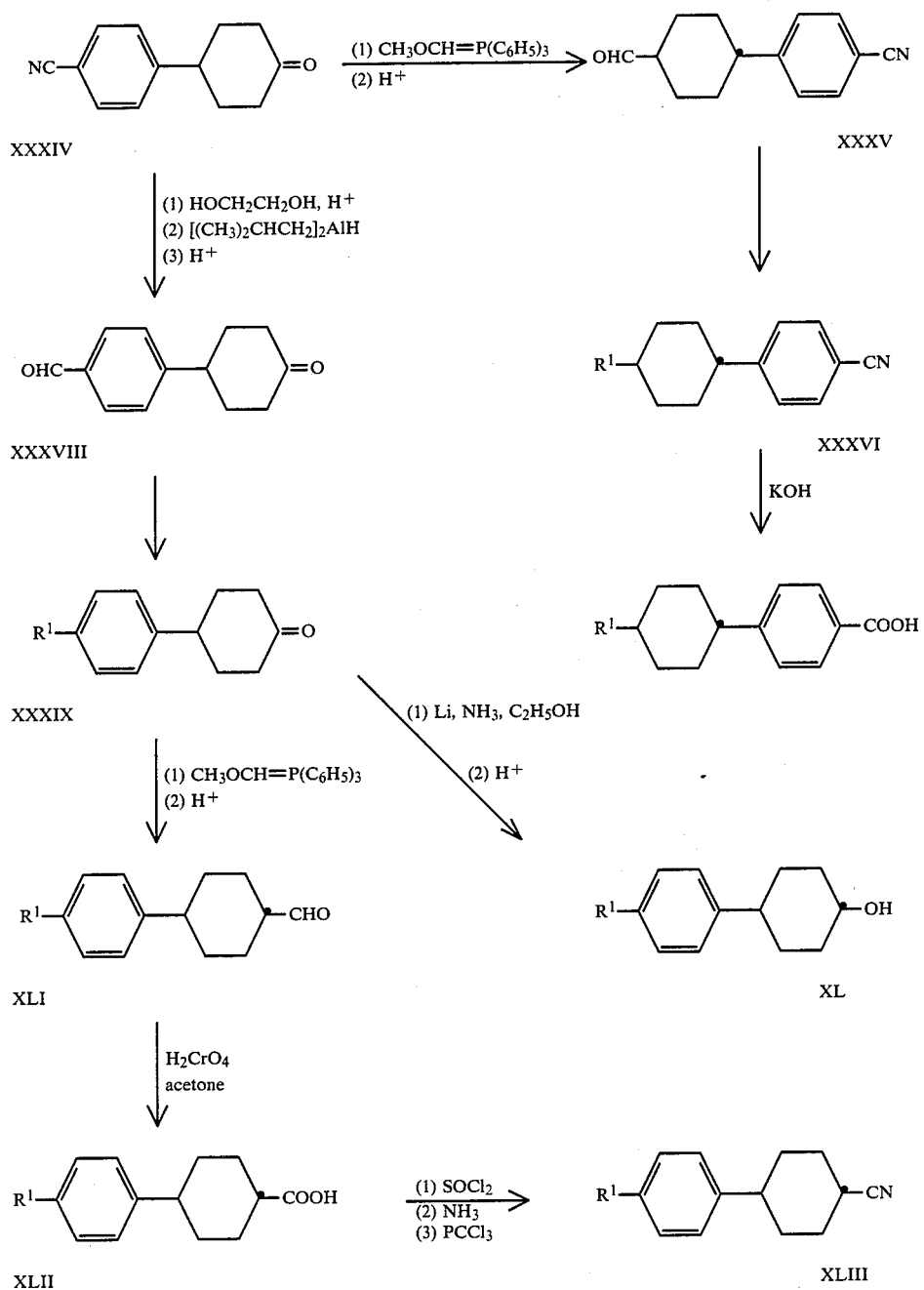

Scheme 4
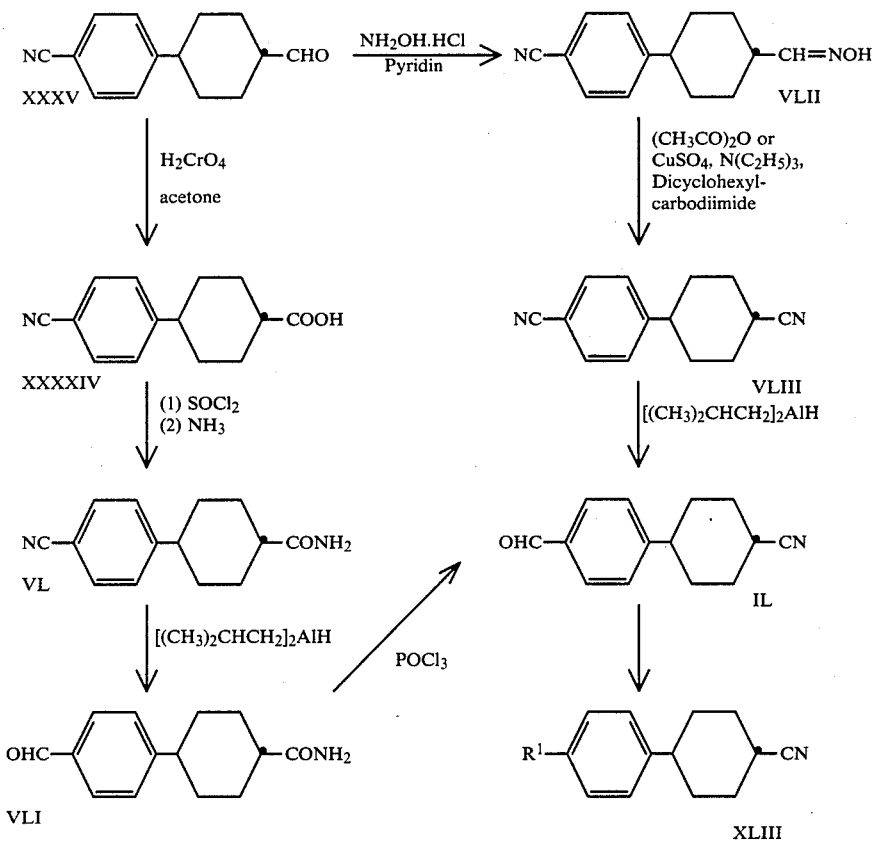
Scheme 5
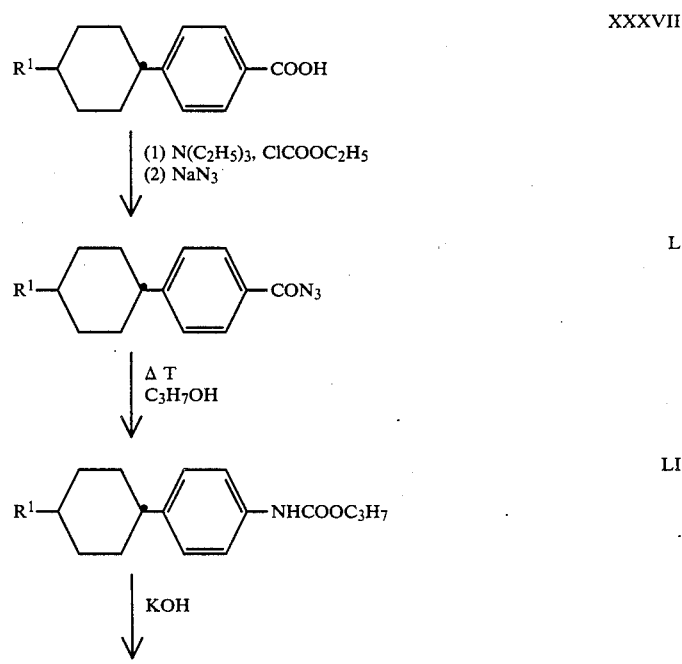

Scheme 5
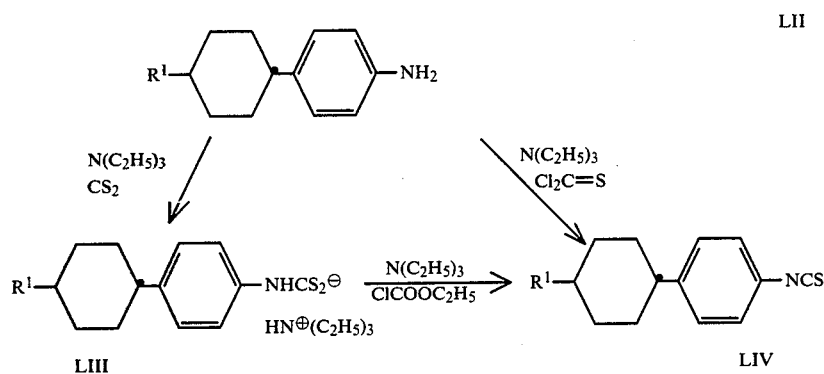
Scheme 6
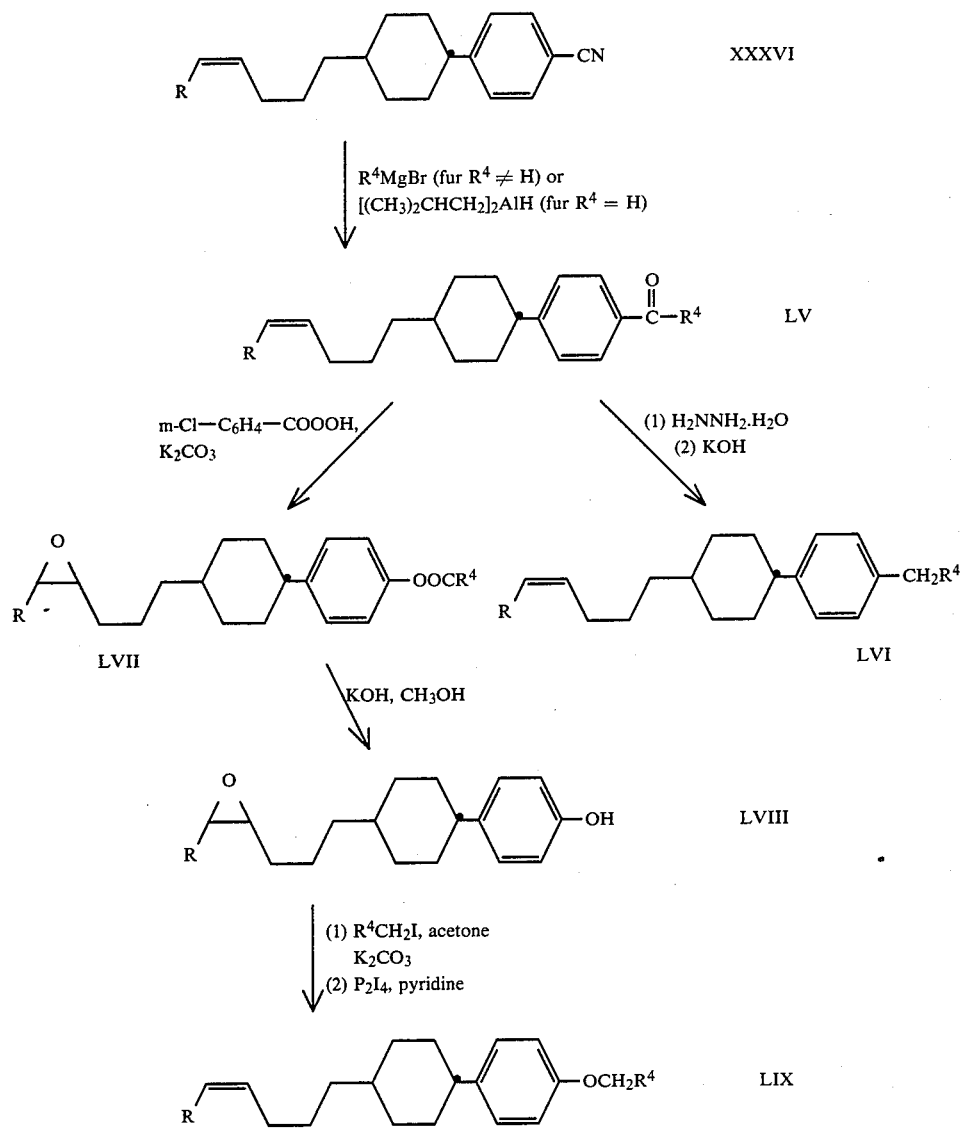

Scheme 7
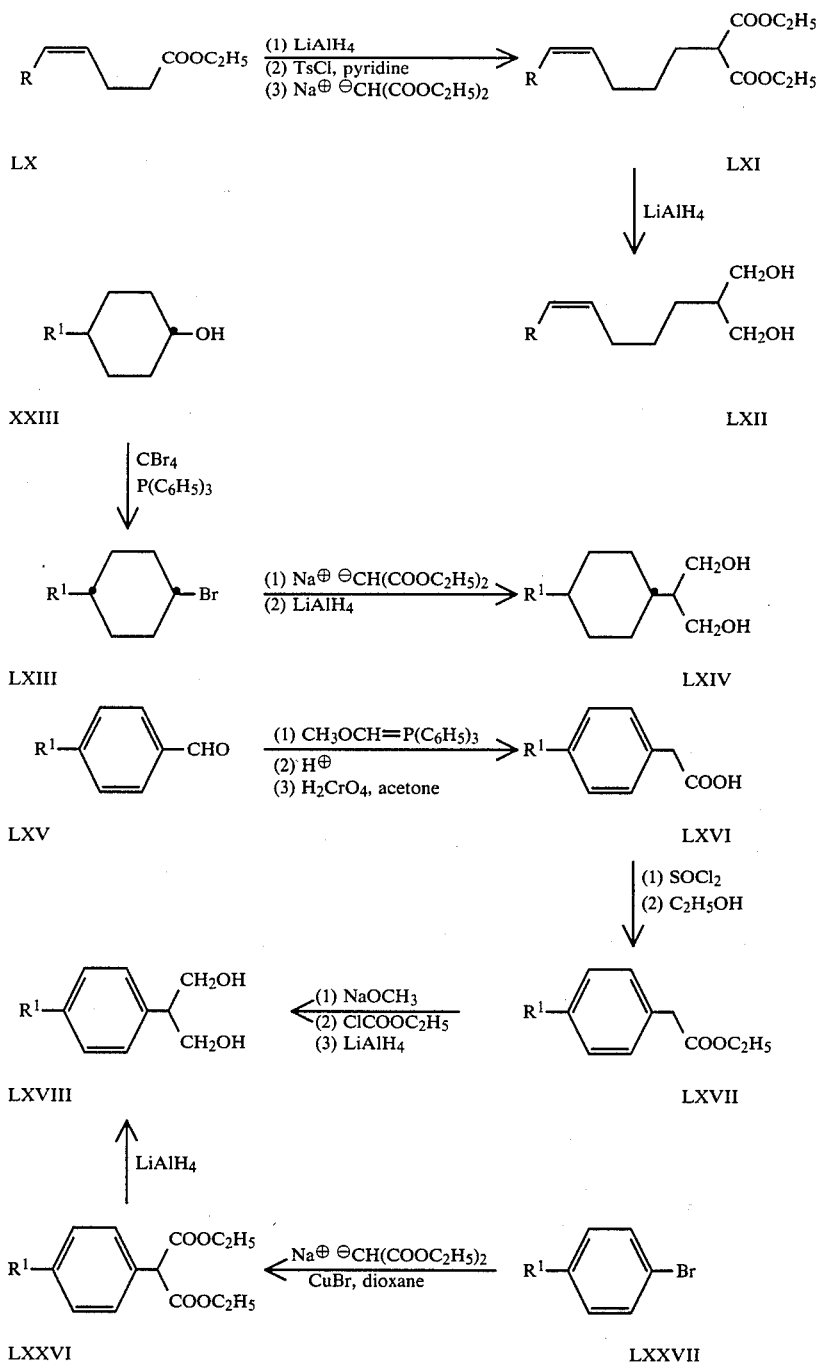
Scheme 8
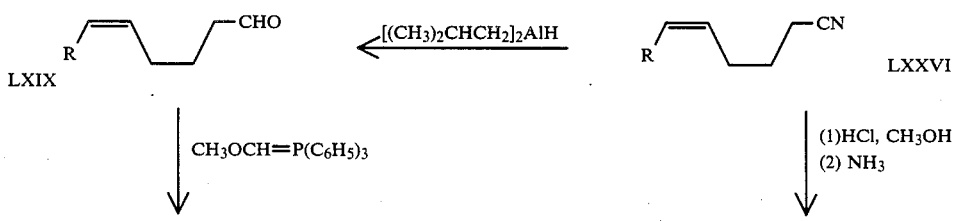

Scheme 8

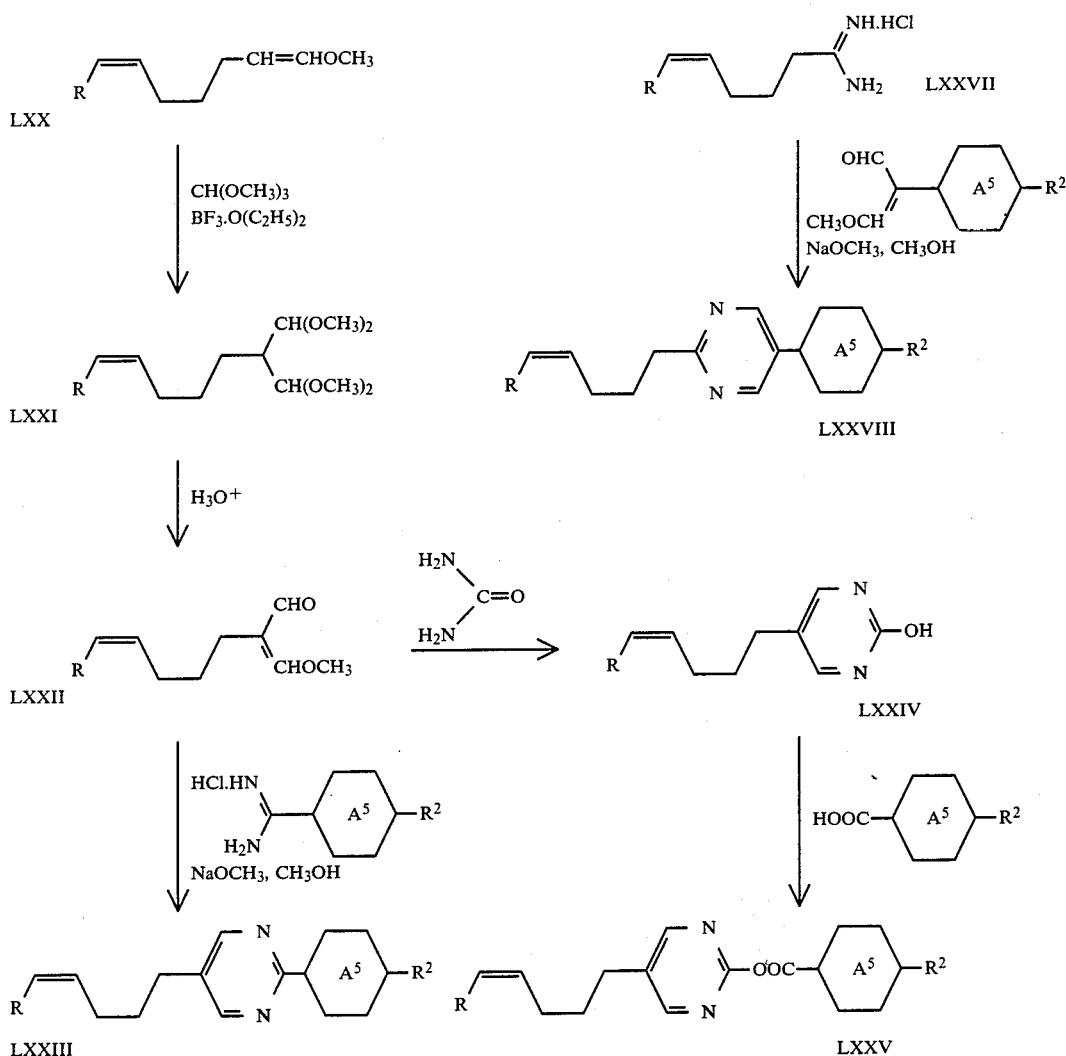

The compounds of formula XX can be converted into corresponding alkenyl compounds in an analogous manner to Scheme 2.

Alkenylphenols can be obtained, for example, by reacting p-hydroxybenzaldehyde with (2-methoxyethoxy)methyl chloride (protection of the hydroxy group, subsequently introducing the alkenyl group according to the methods described in Scheme 1 and cleaving off the protecting group by means of zinc bromide.

4'-Cyano-4-biphenylcarboxyaldehyde can be obtained, for example, by reacting 4-bromobiphenyl firstly with $Cl_2CHOCH_3$ and titanium tetrachloride and then with water and reacting the bromo-aldehyde obtained with copper (I) cyanide in dimethylformamide. The cyano-aldehyde obtained can then be reacted further in an analogous manner to the methods described in Scheme 3.

The introduction of the alkenyl group in accordance with XXXV→XXXVI, XXXVIII→XXXIX and IL→XLIII can be carried out in an analogous manner to the methods shown in Schemes 1 and 2. Further alternatives which permit a shorter synthesis especially in the introduction of 4-alkenyl groups, are illustrated in chemical Examples 8–10 hereinafter.

In the above reactions there are obtained in certain cases mixtures of cis/trans-isomeric cyclohexane derivatives which, however, can be separated in a manner known per se, e.g. by chromatography and/or crystallization. Further, in certain cases there are obtained E/Z mixtures of alkenyl compounds, especially when the alkenyl group is introduced by a Wittig reaction. These can also be separated according to methods known per se, e.g. by chromatography. In this case, silica gel impregnated with silver nitrate has been found to be especially advantageous. If desired, the undesired alkenyl isomer can be converted into the desired isomer, for example by reaction with benzenesulphinic acid or via the epoxide, e.g. by reaction with m-chloroperbenzoic acid in the presence of potassium carbonate, halogenation of the epoxide with triphenylphosphine-bromine in benzene and reduction of the halide with zinc in glacial acetic acid.

Further starting materials can be prepared in an analogous manner to the methods described or according to other methods which are familiar to the person skilled in the art.

The compounds of formulae VIII–XI, XIII, XIV, XVI and XVII in which $R^5$ signifies 1E-alkenyl or 3E-alkenyl are also novel. They can be prepared in an analogous manner to the methods described for the manufacture of the compounds of formula I.

The following mixtures 1–17 are examples of preferred mixtures in accordance with the invention. $V_{10}$ and $V_{50}$ denote the voltage for, respectively, 10% and 50% transmission (in a rotation cell with 0° angle of tilt), $p_o = (V_{50} - V_{10})/V_{10}$ is a measurement for the steepness of the transmission curve and $k_{11}$ (splay) and $k_{33}$ (bend) are elastic constants. $t_{on}$ and $t_{off}$ denote, respectively, the switching-on time and the switching-off time and $\Delta n$ denotes the optical anisotropy. The measurements were carried out at 22° C. unless indicated otherwise.

Mixture 1

| | |
|---|---|
| 7.8 | wt. % of p-(5-butyl-2-pyrimidinyl)benzonitrile, |
| 2.6 | wt. % of p-(5-pentyl-2-pyrimidinyl)benzonitrile, |
| 5.0 | wt. % of p-(5-heptyl-2-pyrimidinyl)benzonitrile, |
| 7.0 | wt. % of 4-ethyl-1-[2-(trans-4-propylcyclohexyl)ethyl]benzene, |
| 9.3 | wt. % of trans-4-butylcyclohexanecarboxylic acid p-ethoxyphenyl ester, |
| 11.5 | wt. % of trans-4-butylcyclohexanecarboxylic acid p-pentyloxyphenyl ester, |
| 8.5 | wt. % of trans-4-pentylcyclohexanecarboxylic acid p-methoxyphenyl ester, |
| 14.4 | wt. % of trans-4-pentylcyclohexanecarboxylic acid p-propoxyphenyl ester, |
| 3.7 | wt. % of 5-(p-butylphenyl)-2-(p-pentylphenyl)pyrimidine, |
| 6.5 | wt. % of 5-(trans-4-ethylcyclohexyl)-2-(p-pentylphenyl)pyrimidine, |
| 4.5 | wt. % of p-[5-(trans-4-ethylcyclohexyl)-2-pyrimidinyl]benzonitrile, |
| 3.4 | wt. % of p-[5-(trans-4-pentylcyclohexyl)-2-pyrimidinyl]benzonitrile, |
| 7.4 | wt. % of 1-[2-(trans-4-butylcyclohexyl)ethyl]-4-(trans-4-pentylcyclohexyl)benzene, |
| 8.4 | wt. % of p-[trans-4-(4-pentenyl)cyclohexyl]benzonitrile; | m.p. below −10° C., cl.p. 71° C., nematic; $V_{10} = 1.729$ V, $p_o = 0.114$, $k_{33}/K_{11} = 0.87$.

Mixture 2

| | |
|---|---|
| 8.2 | wt % of p-(5-butyl-2-pyrimidinyl)benzonitrile, |
| 2.7 | wt % of p-(5-pentyl-2-pyrimidinyl)benzonitrile, |
| 5.2 | wt % of p-(5-heptyl-2-pyrimidinyl)benzonitrile, |
| 6.6 | wt % of 4-ethyl-1-[2-(trans-4-propylcyclohexyl)ethyl]benzene, |
| 9.7 | wt % of trans-4-butylcyclohexanecarboxylic acid p-ethoxyphenyl ester, |
| 12.0 | wt % of trans-4-butylcyclohexanecarboxylic acid p-pentyloxyphenyl ester, |
| 8.9 | wt % of trans-4-pentylcyclohexanecarboxylic acid p-methoxyphenyl ester, |
| 15.1 | wt % of trans-4-pentylcyclohexanecarboxylic acid p-propoxyphenyl ester, |
| 3.8 | wt % of 5-(p-butylphenyl)-2-(p-pentylphenyl)pyrimidine, |
| 6.6 | wt % of 5-(trans-4-ethylcyclohexyl)-2-(p-pentylphenyl)pyrimidine, |
| 4.7 | wt % of [5-(trans-4-ethylcyclohexyl)-2-pyrimidinyl]benzonitrile, |
| 5.0 | wt % of 4-[2-(trans-4-butylcyclohexyl)ethyl]-4′-(trans-4-pentylcyclohexyl)biphenyl, |
| 11.5 | wt % of p-[trans-4-(4-pentenyl)cyclohexyl]benzonitrile; | m.p. below −20° C., cl.p. 63.6° C., nematic; $V_{10} = 1.496$ V, $p_o = 0.120$, $k_{33}/k_{11} = 0.88$.

Mixture 3

| | |
|---|---|
| 11.4 | wt.% of p-(5-butyl-2-pyrimidinyl)benzonitrile, |
| 3.5 | wt. % of p-(5-pentyl-2-pyrimidinyl)benzonitrile, |
| 5.5 | wt. % of p-(5-butyl-2-pyrimidinyl)phenyl isothiocyanate, |
| 14.6 | wt. % of trans-4-butylcyclohexanecarboxylic acid p-ethoxyphenyl ester, |
| 17.8 | wt. % of trans-4-butylcyclohexanecarboxylic acid p-pentyloxyphenyl ester, |
| 12.6 | wt. % of trans-4-pentylcyclohexanecarboxylic acid p-methoxyphenyl ester, |
| 4.5 | wt. % of p-[5-(trans-4-ethylcyclohexyl)-2-pyrimidinyl]phenylisothiocyanate, |
| 16.5 | wt. % of p-[trans-4-(4-pentenyl)cyclohexyl]benzonitrile, |
| 13.6 | wt. % of 4′-[trans-4-(4-pentenyl)cyclohexyl]-4-biphenylcarbonitrile; | m.p. below −25° C., cl.p. 65° C., nematic; $V_{10} = 1.530$ V, $p_o = 0.121$, $k_{33}/k_{11} = 1.03$.

Mixture 4

| | |
|---|---|
| 15.2 | wt. % of p-(trans-4-pentylcyclohexyl)benzonitrile, |
| 2.7 | wt. % of 4-ethoxy-1-(trans-4-propylcyclohexyl)benzene, |
| 7.7 | wt. % of p-(5-butyl-2-pyrimidinyl)benzonitrile, |
| 4.5 | wt. % of p-(5-heptyl-2-pyrimidinyl)benzonitrile, |
| 6.3 | wt. % of 4-ethyl-1-[2-(trans-4-propylcyclohexyl)ethyl]benzene, |
| 9.1 | wt. % of trans-4-butylcyclohexanecarboxylic acid p-ethoxyphenyl ester, |
| 8.3 | wt. % of trans-4-pentylcyclohexanecarboxylic acid p-methoxyphenyl ester, |
| 13.5 | wt. % of trans-4-pentylcyclohexanecarboxylic acid p-propoxyphenyl ester, |
| 5.4 | wt. % of 4-cyano-4′-(trans-4-pentylcyclohexyl)biphenyl, |
| 5.5 | wt. % of p-[5-(trans-4-ethylcyclohexyl)-2-pyrimidinyl]benzonitrile, |
| 11.8 | wt. % of 1-[2-(trans-4-butylcyclohexyl)ethyl]-4-(trans-4-pentylcyclohexyl)benzene, |
| 10/0 | wt. % of p-[trans-4-(2Z-pentenyl)cyclohexyl]benzonitrile; | m.p. below −20° C., cl.p. 60.1° C., nematic; $V_{10} = 1.512$ V, $p_o = 0.125$, $k_{33}/k_{11} = 1.21$.

Mixture 5

| | |
|---|---|
| 12.0 | wt. % of p-(trans-4-pentylcyclohexyl)benzonitrile, |
| 6.3 | wt. % of p-(5-butyl-2-pyrimidinyl)benzonitrile, |
| 1.7 | wt. % of p-(5-pentyl-2-pyrimidinyl)benzonitrile, |
| 3.1 | wt. % of p-(5-heptyl-2-pyrimidinyl)benzonitrile, |
| 10.0 | wt. % of 4-ethyl-1-[2-(trans-4-propylcyclohexyl)ethyl]benzene, |
| 7.5 | wt. % of trans-4-butylcyclohexanecarboxylic acid p-ethoxyphenyl ester, |
| 9.3 | wt. % of trans-4-butylcyclohexanecarboxylic acid p-pentoxyphenyl ester, |
| 6.8 | wt. % of trans-4-pentylcyclohexanecarboxylic acid p-methoxyphenyl ester, |
| 11.1 | wt. % of trans-4-pentylcyclohexanecarboxylic acid p-propoxyphenyl ester, |
| 8.6 | wt. % of 5-(trans-4-ethylcyclohexyl)-2-(p-pentylphenyl)pyrimidine, |
| 3.7 | wt. % of p-[5-(p-butylphenyl)-2-pyrimidinyl]benzonitrile, |
| 3.9 | wt. % of p-[5-(trans-4-ethylcyclohexyl)-2-pyrimidinyl]benzonitrile, |
| 6.0 | wt. % of 1-[2-(trans-4-butylcyclohexyl)ethyl]-4-(trans-4-pentylcyclohexyl)benzene, |
| 10.0 | wt. % of p-[trans-4-(4-pentenyl)cyclohexyl]benzonitrile; | m.p. below −20° C., cl.p. 64° C., nematic; $V_{10} = 1.529$ V, $p_o = 0.124$, $k_{33}/k_{11} = 1.03$.

Mixture 6

| | |
|---|---|
| 5.0 | wt. % of p-[trans-4-(1E-pentenyl)cyclohexyl]phenyl isothiocyanate, |
| 8.3 | wt. % of p-(5-butyl-2-pyrimidinyl)benzonitrile, |

Mixture 6 -continued

| | |
|---|---|
| 2.2 | wt. % of p-(5-pentyl-2-pyrimidinyl)benzonitrile, |
| 4.9 | wt. % of p-(5-heptyl-2-pyrimidinyl)benzonitrile, |
| 4.0 | wt. % of 4-ethyl-1-[2-(trans-4-propylcyclohexyl)ethyl]benzene, |
| 9.7 | wt. % of trans-4-butylcyclohexanecarboxylic acid p-ethoxyphenyl ester, |
| 12.1 | wt. % of trans-4-butylcyclohexanecarboxylic acid p-pentoxyphenyl ester, |
| 8.8 | wt. % of trans-4-pentylcyclohexanecarboxylic acid p-methoxyphenyl ester, |
| 15.4 | wt. % of trans-4-pentylcyclohexancarboxylic acid p-propoxyphenyl ester, |
| 4.0 | wt. % of 5-(p-butylphenyl)-2-(p-pentylphenyl)pyrimidine, |
| 7.0 | wt. % of 5-(trans-4-ethylcyclohexyl)-2-(p-pentylphenyl)pyrimidine, |
| 6.8 | wt. % of p-[5-(trans-4-ethylcyclohexyl)-2-pyrimidinyl]benzonitrile, |
| 11.8 | wt. % of p-[trans-4-(4-pentenyl)cyclohexyl]benzonitrile; | m.p. about $-15°$ C., cl.p. $64.3°$ C., nematic; $V_{10} = 1.580$ V, $p_o = 0.117$, $k_{33}/k_{11} = 0.88$.

Mixture 7

| | |
|---|---|
| 33.40 | wt. % of 4'-pentyl-4-biphenylcarbonitrile, |
| 4.68 | wt. % of 4'-heptyl-4-biphenylcarbonitrile, |
| 14.70 | wt. % of p-(5-butyl-2-pyrimidinyl)benzonitrile, |
| 5.20 | wt. % of p-(5-pentyl-2-pyrimidinyl)benzonitrile, |
| 10.00 | wt. % of p-(5-heptyl-2-pyrimidinyl)benzonitrile, |
| 7.00 | wt. % of 4-ethyl-1-[2-(trans-4-propylcyclohexyl)ethyl]benzene, |
| 6.32 | wt. % of trans-4-butylcyclohexanecarboxylic acid p-ethoxyphenyl ester, |
| 4.00 | wt. % of 5-(p-butylphenyl)-2-(p-pentylphenyl)pyrimidine, |
| 6.00 | wt. % of 5-(trans-4-ethylcyclohexyl)-2-(p-pentylphenyl)pyrimidine, |
| 8.70 | wt. % of 4'-[trans-4-(4-pentenyl)cyclohexyl]-4-biphenylcarbonitrile; | m.p. below $-25°$ C., cl.p. $61°$ C., nematic; $V_{10} = 1.31$ V, $p_o = 0.132$, $k_{33}/k_{11} = 1.14$; $\Delta n = 0.183$.

Mixture 8

| | |
|---|---|
| 11.38 | wt. % of p-(5-butyl-2-pyrimidinyl)benzonitrile, |
| 3.44 | wt. % of p-(5-pentyl-2-pyrimidinyl)benzonitrile, |
| 6.70 | wt. % of p-(5-heptyl-2-pyrimidinyl)benzonitrile, |
| 13.56 | wt. % of trans-4-butylcyclohexanecarboxylic acid p-ethoxyphenyl ester, |
| 17.80 | wt. % of trans-4-butylcyclohexanecarboxylic acid p-pentyloxyphenyl ester, |
| 12.51 | wt. % of trans-4-pentylcyclohexanecarboxylic acid p-methoxyphenyl ester, |
| 5.71 | wt. % of p-[5-(trans-4-pentylcyclohexyl)-2-pyrimidinyl]benzonitrile |
| 16.49 | wt. % of p-[trans-4-(4-pentenyl)cyclohexyl]benzonitrile, |
| 12.41 | wt. % of 4'-[trans-4-(4-pentenyl)cyclohexyl]-4-biphenylcarbonitrile; | m.p. below $-25°$ C., cl.p. $69°$ C., nematic; $V_{10} = 1.39$ V, $p_o 0.124$, $k_{33}/k_{11} = 1.09$; $\Delta n = 0.129$.

Mixture 9

| | |
|---|---|
| 11.49 | wt. % of p-(5-butyl-2-pyrimidinyl)benzonitrile, |
| 3.48 | wt. % of p-(5-pentyl-2-pyrimidinyl)benzonitrile, |
| 6.76 | wt. % of p-(5-heptyl-2-pyrimidinyl)benzonitrile, |
| 13.68 | wt. % of trans-4-butylcyclohexanecarboxylic acid p-ethoxyphenyl ester, |
| 17.97 | wt. % of trans-4-butylcyclohexanecarboxylic acid p-pentyloxyphenyl ester, |
| 5.76 | wt. % of p-[5-(trans-4-pentylcyclohexyl)-2-pyrimidinyl]benzonitrile, |
| 16.65 | wt. % of p-[trans-4-(4-pentenyl)cyclohexyl]benzonitrile, |
| 11.68 | wt. % of p-[2-(trans-4-(4-pentenyl)cyclohexyl)ethyl]benzonitrile, |
| 12.53 | wt. % of 4'-[trans-4-(4-pentenyl)cyclohexyl]-4-biphenylcarbonitrile; | m.p. below $-25°$ C., cl.p. $63°$ C., nematic; $V_{10} = 1.318$ V, $p_o = 0.121$, $k_{33}/k_{11} = 1.11$; $\Delta n = 0.127$.

Mixture 10

| | |
|---|---|
| 11.59 | wt. % of p-(5-butyl-2-pyrimidinyl)benzonitrile, |
| 3.51 | wt. % of p-(5-pentyl-2-pyrimidinyl)benzonitrile, |
| 6.82 | wt. % of p-(5-heptyl-2-pyrimidinyl)benzonitrile, |
| 10.86 | wt. % of p-(5-pentyl-m-dioxan-2-yl)benzonitrile, |
| 13.81 | wt. % of trans-4-butylcyclohexanecarboxylic acid p-ethoxyphenyl ester, |
| 18.14 | wt. % of trans-4-butylcyclohexanecarboxylic acid p-pentyloxyphenyl ester, |
| 5.82 | wt. % of p-[5-(trans-4-pentylcyclohexyl)-2-pyrimidinyl]benzonitrile, |
| 16.80 | wt. % of p-[trans-4-(4-pentenyl)cyclohexyl]benzonitrile, |
| 12.65 | wt. % of 4'-[trans-4-(4-pentenyl)cyclohexyl]-4-biphenylcarbonitrile; | m.p. below $-25°$ C., cl.p. $68°$ C., nematic; $V_{10} = 1.272$ V, $p_o = 0.129$, $k_{33}/k_{11} = 1.13$; $\Delta n = 0.135$.

Mixture 11

| | |
|---|---|
| 11.31 | wt. % of p-(5-butyl-2-pyrimidinyl)benzonitrile, |
| 3.42 | wt. % of p-(5-pentyl-2-pyrimidinyl)benzonitrile, |
| 5.71 | wt. % of p-(5-heptyl-2-pyrimidinyl)benzonitrile, |
| 13.47 | wt. % of trans-4-butylcyclohexanecarboxylic acid p-ethoxyphenyl ester, |
| 17.69 | wt. % of trans-4-butylcyclohexanecarboxylic acid p-pentyloxyphenyl ester, |
| 5.67 | wt. % of p-[5-(trans-4-pentylcyclohexyl)-2-pyrimidinyl]benzonitrile, |
| 16.39 | wt. % of p-[trans-4-(4-pentenyl)cyclohexyl]benzonitrile, |
| 14.00 | wt. % of trans-4-(4-pentenyl)cyclohexanecarboxylic acid p-ethoxyphenyl ester, |
| 12.34 | wt. % of 4'-[trans-4-(4-pentenyl)cyclohexyl]-4-biphenylcarbonitrile; | m.p. below $-25°$ C., cl.p. $66°$ C., nematic; $V_{10} = 1.342$ V, $p_o = 0.119$, $k_{33}/k_{11} = 1.01$, $\Delta n = 0.128$.

Mixture 12

| | |
|---|---|
| 10.70 | wt. % of p-(5-butyl-2-pyrimidinyl)benzonitrile, |
| 3.02 | wt. % of p-(5-pentyl-2-pyrimidinyl)benzonitrile, |
| 6.71 | wt. % of p-(5-heptyl-2-pyrimidinyl)benzonitrile, |
| 12.81 | wt. % of trans-4-butylcyclohexanecarboxylic acid p-ethoxyphenyl ester, |
| 16.67 | wt. % of trans-4-butylcyclohexanecarboxylic acid p-pentyloxyphenyl ester, |
| 11.90 | wt. % of trans-4-pentylcyclohexanecarboxylic acid p-methoxyphenyl ester, |
| 5.01 | wt. % of p-[5-(trans-4-pentylcyclohexyl)-2-pyrimidinyl]benzonitrile, |
| 10.00 | wt. % of p-[trans-4-(4-pentenyl)cyclohexyl]benzonitrile, |
| 10.30 | wt. % of p-[trans-4-(4-pentenyl)cyclohexyl]phenyl isothiocyanate, |
| 12.88 | wt. % of 4'-[trans-4-(4-pentenyl)cyclohexyl]-4-biphenylcarbonitrile; | m.p. below $-20°$ C., cl.p. $67°$ C., nematic; $V_{10} = 1.44$ V, $p_o = 0.118$

Mixture 13

| | |
|---|---|
| 3.50 | wt. % of 4'-propyl-4-biphenylcarbonitrile, |
| 17.10 | wt. % of 4'-pentyl-4-biphenylcarbonitrile, |
| 14.47 | wt. % of 4-ethoxy-1-[2-(trans-4-propylcyclohexyl)ethyl]benzene, |
| 19.94 | wt. % of 4-ethoxy-1-[2-(trans-4-pentylcyclohexyl)ethyl]benzene, |
| 5.15 | wt. % of 4''-pentyl-4-cyano-p-terphenyl, |

Mixture 13

| | |
|---|---|
| 5.25 | wt. % of 4'-(trans-4-pentylcyclohexyl)-4-biphenylcarbonitrile, |
| 11.51 | wt. % of 1-[2-(trans-4-butylcyclohexyl)ethyl]-4-(trans-4-pentylcyclohexyl)benzene, |
| 5.38 | wt. % of 4'-[2-(trans-4-butylcyclohexyl)ethyl]-4-(trans-4-pentylcyclohexyl)biphenyl, |
| 7.70 | wt. % of 4'-[2-(trans-4-butylcyclohexyl)ethyl]-4-(trans-4-pentylcyclohexyl)-1,1'-ethylenedibenzene, |
| 10.00 | wt. % of trans-4-(4-pentenyl)cyclohexanecarboxylic acid m-fluoro-p-cyanophenyl ester; | m.p. below $-20°$ C., cl.p. $81°$ C., nematic; $V_{10} = 2.40$ V, $p_o = 0.120$; $\Delta n = 0.139$. $V_{10} = 2.80$ V for the mixture without trans-4-(4-pentenyl)cyclohexanecarboxylic acid m-fluoro-p-cyanophenyl ester.

Mixture 14

| | |
|---|---|
| 11.58 | wt. % of p-(5-butyl-2-pyrimidinyl)benzonitrile, |
| 3.50 | wt. % of p-(5-pentyl-2-pyrimidinyl)benzonitrile, |
| 6.82 | wt. % of p-(5-heptyl-2-pyrimidinyl)benzonitrile, |
| 14.86 | wt. % of trans-4-butylcyclohexanecarboxylic acid p-ethoxyphenyl ester, |
| 13.80 | wt. % of trans-4-pentylcyclohexanecarboxylic acid p-methoxyphenyl ester, |
| 17.99 | wt. % of trans-4-butylcyclohexanecarboxylic acid trans-4-butylcyclohexyl ester, |
| 17.67 | wt. % of p-[trans-4-(4-pentenyl)cyclohexyl]benzonitrile, |
| 13.78 | wt. % of 4'-[trans-4-(4-pentenyl)cyclohexyl]-4-biphenylcarbonitrile; | m.p. below $-25°$ C., cl.p. $54°$ C., nematic; $V_{10} = 1.259$, $p_o = 0.119$, $k_{33}/k_{11} = 1.14$; $\Delta n = 0.112$.

Mixture 15

| | |
|---|---|
| 9.54 | wt. % of p-[trans-4-(3-butenyl)cyclohexyl]benzonitrile, |
| 5.05 | wt. % of p-[trans-4-(3E-pentenyl)cyclohexyl]benzonitrile, |
| 12.92 | wt. % of p-(trans-4-propylcyclohexyl)phenyl isothiocyanate, |
| 4.94 | wt. % of 4-ethoxy-1-(trans-4-propylcyclohexyl)benzene, |
| 4.16 | wt. % of 4-ethyl-1-[2-(trans-4-propylcyclohexyl)ethyl]benzene, |
| 16.58 | wt. % of 4-ethoxy-1-[2-(trans-4-pentylcyclohexyl)ethyl]benzene, |
| 3.14 | wt. % of 4'[trans-4-(3-butenyl)cyclohexyl]-4-biphenylcarbonitrile, |
| 1.64 | wt. % of 4'-[trans-4-(3E-pentenyl)cyclohexyl]-4-biphenylcarbonitrile, |
| 6.62 | wt. % of 4'-ethyl-4-[trans-4-(3E-pentenyl)cyclohexyl]-biphenyl, |
| 8.63 | wt. % of 4'-propyl-4-[trans-4-(3E-pentenyl)cyclohexyl]-biphenyl, |
| 9.88 | wt. % of 1-[2-(trans-4-butylcyclohexyl)ethyl]-4-(trans-4-pentylcyclohexyl)benzene, |
| 4.94 | wt. % of 4'-[2-(trans-4-butylcyclohexyl)ethyl]-4-(trans-4-pentylcyclohexyl)biphenyl, |
| 5.98 | wt. % of 4'-[2-(trans-4-butylcyclohexyl)ethyl]-4-(trans-4-pentylcyclohexyl)-1,1'-ethylenedibenzene, |
| 5.98 | wt. % of 4-ethyl-1-[trans-4-(4-pentenyl)cyclohexyl]benzene; | m.p. below $-30°$ C., cl.p. $86°$ C., nematic; $V_{10} = 2.803$ V, $p_o = 0.118$; $t_{on}(22°$ C.$) = 27$ ms, $t_{off}(22°$ C.$) = 35$ ms; $t_{on}(-20°$ C.$) = 345$ ms, $t_{off}(-20°$ C.$) = 386$ ms.

Mixture 16

| | |
|---|---|
| 15.22 | wt. % of p-(trans-4-pentylcyclohexyl)benzonitrile, |
| 2.70 | wt. % of 4-ethoxy-1-(trans-4-propylcyclohexyl)benzene, |
| 7.71 | wt. % of p-(5-butyl-2-pyrimidinyl)benzonitrile, |
| 4.54 | wt. % of p-(5-heptyl-2-pyrimidinyl)benzonitrile, |
| 6.30 | wt. % of 4-ethyl-1-[2-(trans-4-propylcyclohexyl)ethyl]benzene, |
| 9.06 | wt. % of trans-4-butylcyclohexanecarboxylic acid p-ethoxyphenyl ester, |
| 8.23 | wt. % of trans-4-pentylcyclohexanecarboxylic acid p-ethoxyphenyl ester, |
| 13.50 | wt. % of trans-4-pentylcyclohexanecarboxylic acid p-propyloxyphenyl ester, |
| 5.39 | wt. % of 4'-(trans-4-pentylcyclohexyl)-4-biphenylcarbonitrile, |
| 5.53 | wt. % of p-[5-(trans-4-ethylcyclohexyl)-2-pyrimidinyl]-benzonitrile, |
| 11.82 | wt. % of 1-[2-(trans-4-butylcyclohexyl)ethyl]-4-(trans-4-pentylcyclohexyl)benzene, |
| 10.00 | wt. % of trans-5-(4-pentenyl)-2-(p-butoxyphenyl)-m-dioxane; | m.p. below $-20°$ C., cl.p. $67°$ C., nematic; $V_{10} = 1.616$ V, $p_o = 0.126$, $k_{33}k_{11} = 1.07$. $V_{10} = 1.71$ V, $p_o = 0.128$ and $k_{33}/k_{11} = 1.19$ for the corresponding mixture without trans-5-(4-pentenyl)-2-(p-butoxyphenyl)-m-dioxane.

Mixture 17

| | |
|---|---|
| 7 | wt. % of 4'-methyl-4-pentylbiphenyl, |
| 10 | wt. % of p-(5-butyl-2-pyrimidinyl)benzonitrile |
| 12 | wt. % of trans-4-butylcyclohexanecarboxylic acid p-ethoxyphenyl ester, |
| 11 | wt. % of trans-4-pentylcyclohexanecarboxylic acid p-methoxyphenyl ester, |
| 17 | wt. % of trans-4-pentylcyclohexanecarboxylic trans-4-propylcyclohexyl ester, |
| 3 | wt. % of 5-(p-butylphenyl)-2-(p-pentylphenyl)pyrimidine, |
| 5 | wt. % of 5-(trans-4-ethylcyclohexyl)-2-(p-pentylphenyl)pyrimidine, |
| 12 | wt. % of p-[trans-4-[4-pentenyl)cyclohexyl]benzonitrile, |
| 12 | wt. % of trans-4-(4-pentenyl)cyclohexanecarboxylic acid p-ethoxyphenyl ester, |
| 11 | wt. % of 4'-[trans-4-(4-pentenyl)cyclohexyl]-4-biphenylcarbonitrile; | m.p. below $-20°$ C., cl.p. $60°$ C., nematic; $V_{10} = 1.641$ V, $p_o = 0.112$.

The manufacture of the compounds of formula I is illustrated further by the following Examples. C signifies a crystalline phase, S signifies a smectic phase, $S_A$ signifies a smectic A phase, $S_B$ signifies a smectic B phase, N signifies a nematic phase and I signifies the isotropic phase. Unless otherwise stated, percentages and ratios relating to solvent mixtures are expressed in volume, purity data determined by gas chromatography are expressed in area % and the remaining percentages and ratios are expressed in weight, temperatures are in degrees Celsius (°C), normal pressure is about 1 atmosphere and room temperature is about 23° C. The petroleum ether is a well known mixture of low-boiling hydrocarbons. Unless otherwise indicated (e.g., by use of a present tense verb) the Examples were carried out as written.

EXAMPLE 1

(a) 10.4 g of triphenyl-methoxymethyl-phosphonium chloride were suspended in 60 ml of t-butyl methyl ether while gassing with argon in a sulphonation flask equipped with a thermometer, a mechanical stirrer, a dropping funnel and a solid substance addition tube and the suspension was treated with 3.6 g of solid potassium t-butylate at $-10°$ C. within 10 minutes. After completion of the addition the mixture was stirred for a further 30 minutes at $-10°$ C. then the deep orange, heterogeneous reaction mixture was treated dropwise at 0° C. with a solution of 4.2 g of 4-(p-cyanophenyl)cyclohexanone in 50 ml of absolute tetrahydrofuran. The reaction mixture was subsequently stirred for a futher 2 hours at room temperature, then poured into 500 ml of hexane and filtered. Low-pressure chromatography (0.5 bar) of the concentrated residue (7.1 g) on silica gel with ethyl acetate/petroleum ether (vol. 5:95) gave 4.5 g (94%) of p-[4-(methoxymethylene)cyclohexyl]benzonitrile as a colourless oil; purity 95%, Rf-value (ethyl acetate/petroleum ether vol. 1:9) 0.30.

(b) A mixture of 4.2 g of p-[4-methoxymethylene)cyclohexyl]benzonitrile and 100 ml of tetrahydrofuran/2N hydrochloric acid (vol. 4:1) was heated to reflux for 30 minutes in a round flask. The reaction mixture was subsequently poured into 100 ml of water and extracted three times with 100 ml of diethyl ether each time. The organic phases were washed once with 100 ml of water, dried over magnesium sulphate and concentrated. There were obtained 3.9 g (100%) of 4-(p-cyanophenyl)cyclohexanecarboxaldehyde as a colourless oil which was used in the next step without further purification; trans/cis ratio about 3:1, Rf-value (ethyl acetate/petroleum ether vol. 3:7) 0.41. By crystallization from hexane there could be obtained pure trans-4-(p-cyanophenyl)cyclohexanecarboxaldehyde; m.p. 57.1° C.

(c) A suspension of 29.0 g of methoxymethyl-triphenylphosphonium chloride in 200 ml of t-butyl methyl ether was treated within 10 minutes with 9.7 g of potassium t-butylate while gassing with argon at −10° C. and the mixture was stirred for a further 1 hour. The mixture was then treated dropwise within 15 minutes at 10° C. with a solution of 12.0 g of trans-4-(p-cyanophenyl)cyclohexanecarboxaldehyde in 90 ml of t-butyl methyl ether and the resulting mixture was stirred for a further 1 hour at 0° C. The reaction mixture was subsequently poured into 150 ml of water and extracted three times with 150 ml of diethyl ether each time. The organic phases were washed twice with 100 ml of water each time, dried over magnesium sulphate and concentrated. The resulting, viscous oil was dissolved in 20 ml of ethyl acetate and the clear solution was diluted with 300 ml of petroleum ether and left to stand for 10 minutes at −20° C. The precipitated triphenylphosphine oxide was subsequently filtered off and the filtrate was concentrated to dryness. Low-pressure chromatography (0.5 bar) of the residue (16.3 g) on silica gel with ethyl acetate/petroleum ether (vol. 5:95) gave 10.1 g (74%) of p-[trans-4-(2-methoxyvinyl)cyclohexyl]benzonitrile as colourless crystals; Rf-value (ethyl acetate/petroleum ether vol. 10:90) 0.32.

(d) A solution of 10.1 g of p-[trans-4-(2-methoxyvinyl)cyclohexyl]benzonitrile in 200 ml of tetrahydrofuran/2N hydrochloric acid (vol. 4:1) was heated to reflux for 1 hour. The reaction mixture was subsequently poured into 200 ml of water and extracted three times with 150 ml of diethyl ether each time. The organic phases were washed twice with 100 ml of water each time, dried over magnesium sulphate and concentrated, whereby 9.8 g of [trans-4-(p-cyanophenyl)cyclohexyl]acetaldehyde were obtained as light yellowish crystals (purity 98.7%). Recrystallization of a sample from hexane/t-butyl methyl ether (vol. 1:1) gave pure aldehyde with m.p. 43.4° C.

(e) A suspension of 4.5 g of methoxymethyl-triphenylphosphonium chloride in 40 ml of t-butyl methyl ether was treated within 3 minutes with 1.5 g of potassium t-butylate while gassing with argon at −10° C. and the solution was stirred for a further 1 hour at 0°-5° C. The suspension was then treated dropwise within 5 minutes at 0° C. with a solution of 2.0 g of [trans-4-(p-cyanophenyl)cyclohexyl]acetaldehyde in 20 ml of t-butyl methyl ether and the mixture was stirred for a further 2 hours at room temperature. The reaction mixture was subsequently poured into 100 ml of water and extracted three times with 100 ml of diethyl ether each time. The organic phased were washed twice with 100 ml of water each time, dried over magnesium sulphate and concentrated. The resulting, viscous oil was dissolved in 15 ml of ethyl acetate and the clear solution was treated with 250 ml of petroleum ether. After leaving to stand for 10 minutes at −20° C. the precipitated triphenylphosphine oxide was filtered off and the filtrate was concentrated to dryness. Low-pressure chromatography (0.5 bar) of the residue (3.3 g) on silica gel with ethyl acetate/petroleum ether (vol. 5:95) gave 2.04 g (91%) of p-[trans-4-(3-methoxy-2-propenyl)cyclohexyl]benzonitrile as a colourless oil; Rf-value (ethyl acetate/petroleum ether vol. 10:90) 0.33.

(f) A solution of 2.04 g of p-[trans-4-(3-methoxy-2-propenyl)cyclohexyl]benzonitrile in 100 ml of tetrahydrofuran/2N hydrochloric acid (vol. 4:1) was heated to reflux for 1 hour. The reaction mixture was subsequently poured into 100 ml of water and extracted three times with 100 ml of diethyl ether each time. The organic phases were washed twice with 100 ml of water each time, dried over magnesium sulphate and concentrated, whereby 1.9 g (99%) of 3-[trans-4-(p-cyanophenyl)cyclohexyl]propionaldehyde were obtained as colourless crystals; Rf-value (ethyl acetate/petroleum ether vol. 10:90) 0.15.

(g) A suspension of 6.4 g of methoxymethyl-triphenylphosphonium chloride in 80 ml of t-butyl methyl ether was treated within 3 minutes with 2.1 g of potassium t-butylate while gassing with argon at 0° C. and the mixture was stirred for a further 1 hour at 0°-5° C. The mixture was then treated dropwise within 5 minutes at 0° C. with a solution of 3.0 g of 3-[trans-4-(p-cyanophenyl)cyclohexyl]propionaldehyde in 20 ml of t-butyl methyl ether and the resulting mixture was stirred for a further 2 hours at room temperature. The reaction mixture was subsequently poured into 100 ml of water and extracted three times with 100 ml of diethyl ether each time. The organic phases were washed twice with 100 ml of water each time, dried over magnesium sulphate and concentrated. The residue was dissolved in 15 ml of ethyl acetate and the clear solution was treated with 250 ml of petroleum ether. After leaving to stand for 10 minutes at −20° C. the precipitated triphenylphosphine oxide was filtered off and the filtrate was concentrated to dryness. Low-pressure chromatography (0.5 bar) of the residue (5.5 g) on silica gel with ethyl acetate/petroleum ether (vol. 5:95) gave 2.95 g (88%) of p-[trans-4-(4-methoxy-3-butenyl)cyclohexyl]benzonitrile as colourless crystals.

(h) A solution of 2.95 g of p-[trans-4-(4-methoxy-3-butenyl)cyclohexyl]benzonitrile in 100 ml of tetrahydrofuran/2N hydrochloric acid (vol. 4:1) was heated to reflux for 15 minutes. The reaction mixture was subsequently poured into 100 ml of water and extracted three times with 100 ml of diethyl ether each time. The organic phases were washed twice with 100 ml of water each time, dried over magnesium sulphate and concentrated, whereby 2.6 g (93%) of 4-[trans-4-(p-cyanophenyl)cyclohexyl]butyraldehyde were obtained as a slightly yellowish oil; Rf-value (toluene/ethyl acetate vol. 95:5) 0.23.

(i) A suspension of 7.34 g of methyl-triphenylphosphonium bromide in 90 ml of t-butyl methyl ether was treated within 2 minutes with 2.3 g of potassium t-butylate while gassing with argon at 0° C. and the mixture was stirred for a further 1 hour at room temperature.

Thereafter, the mixture was treated dropwise within 5 minutes with a solution of 3.5 g of 4-[trans-4-(p-cyanophenyl)cyclohexyl]butyraldehyde in 20 ml of t-butyl methyl ether and the resulting mixture was stirred for a further 20 hours at room temperature. The reaction mixture was subsequently poured into 100 ml of water and extracted three times with 100 ml of diethyl ether each time. The organic phases were washed twice with 100 ml of water each time, dried over magnesium sulphate and concentrated. The residue was dissolved in 15 ml of ethyl acetate and the clear solution was treated with 250 ml of petroleum ether. After leaving to stand for 10 minutes at −20° C. the precipitated triphenylphosphine oxide was filtered off and the filtrate was concentrated to dryness. Low-pressure chromatography (0.5 bar) of the oily residue (4.8 g) on silica gel with ethyl acetate/petroleum ether (vol. 5:95) gave 3.1 g (89%) of a yellowish oil. Recrystallization at −20° C. from methanol finally gave 2.76 g (80%) of p-[trans-4-(4-pentenyl)cyclohexyl]benzonitrile as colourless crystals; m.p. (C-I) 29.8° C., cl.p. (N-I) 10.2° C.

The following compounds can be manufactured in an analogous manner:

4'-(trans-4-Allylcyclohexyl)-4-biphenylcarbonitrile; m.p. (C-N) 107.7° C., cl.p. (N-I) 181.7° C., 4'-[trans-4-(4-pentenyl)cyclohexyl]-4-biphenylcarbonitrile; m.p. (C-N) 77.4° C., cl.p. (N-I) 200.8° C.

EXAMPLE 2

(a) A suspension of 5.1 g of propyl-triphenylphosphonium bromide in 80 ml of t-butyl methyl ether was treated within 5 minutes with 1.48 g of potassium t-butylate while gassing with argon at −10° C. and the mixture was stirred at room temperature for a further 60 minutes. Thereafter, the mixture was treated within 5 minutes at 0° C. with a solution of 2.0 g of [trans-4-(p-cyanophenyl)cyclohexyl]acetaldehyde in 25 ml of t-butyl methyl ether and the resulting mixture was stirred for a further 45 minutes at room temperature. The reaction mixture was subsequently poured into 100 ml of water and extracted three times with 100 ml of diethyl ether each time. The organic phases were washed twice with 100 ml of water each time, dried over magnesium sulphate and concentrated. The residue was dissolved in 20 ml of ethyl acetate and the solution was treated with 250 ml of petroleum ether. After leaving to stand for 10 minutes at −20° C. the precipitated triphenylphosphine oxide was filtered off and the filtrate was concentrated to dryness. Low-pressure chromatography (0.5 bar) of the yellowish, oily residue (3.33 g) on silica gel with ethyl acetate/petroleum ether (vol. 3:97) gave 2.1 g of p-[trans-4-(2-pentenyl)cyclohexyl]benzonitrile as a colourless oil containing 92.7% of p-[trans-2-(2Z-pentenyl)cyclohexyl]benzonitrile and 6.6% of p-[trans-4-(2E-pentenyl)cyclohexyl]benzonitrile. The material was reacted further without additional purification. If desired, however, this mixture of isomers can be separated by chromatography on silica gel coated with silver nitrate (as illustrated in paragraph d).

(b) A solution of 1.59 g of 90 percent m-chloroperbenzoic acid in 60 ml of methylene chloride was treated with 4.0 g of ground potassium carbonate. The suspension obtained was treated dropwise within 5 minutes at 0° C. with a solution of 2.1 g of p-[trans-4-(2-pentenyl)-cyclohexyl]benzonitrile (containing 92.7% 2Z-isomer and 6.6% 2E-isomer) in 20 ml of methylene chloride and the mixture was then stirred for a further 3 hours at rooom temperature, whereby a further 0.8 g of m-chloroperbenzoic acid was added after 1 hour and after 2 hours. The reaction mixture was subsequently poured into 150 ml of 10 percent sodium thiosulphate solution and extracted three times with 100 ml of methylene chloride each time. The organic phases were washed with 100 ml of 10 percent sodium thiosulphate solution and with 100 ml of saturated sodium carbonate solution, dried over magnesium sulphate and concentrated. This gave 2.2 g (99%) of p-[trans-4-(2,3-epoxypentyl)cyclohexyl]benzonitrile as colourless crystals; Rf-value (ethyl acetate/petroleum ether vol. 10:90) 0.15. This material was processed without additional purification.

(c) A solution of 2.6 g of triphenylphosphine in 30 ml of methylene chloride was treated dropwise at 0° C. with a solution of 0.519 ml of bromine in 20 ml of methylene chloride until a slight yellow colour persisted. The yellow suspension obtained was cautiously concentrated to dryness on a rotary evaporator and the yellowish, crystalline residue was dried in a high vacuum (0.5 Torr) at room temperature for 1 hour. The triphenylphosphine-bromine obtained was suspended in 50 ml of toluene and the suspension was concentrated to dryness on a rotary evaporator. Thereafter, the residue was suspended in 30 ml of toluene, the suspension was treated with a solution of 2.2 g of p-[trans-4-(2,3-epoxypentyl)cyclohexyl]benzonitrile in 10 ml of toluene and the mixture was stirred for 2 hours at 80° C. bath temperature. Low-pressure chromatography (0.5 bar) of the cooled reaction mixture on silica gel with toluene gave 2.83 g (84%) of p-[trans-4-(2,3-dibromopentyl)cyclohexyl]benzonitrile as a yellowish oil (containing 66.6% erythro form and 32.8% threo form); Rf-value (ethyl acetate/petroleum ether vol. 10:90) 0.33. This material was processed without additional purification.

(d) A solution of 1.98 g of p-[trans-4-(2,3-dibromopentyl)cyclohexyl]benzonitrile (erythro/threo 66.6:32.8) in 30 ml of glacial acetic acid was treated at room temperature with 2.0 g of zinc powder while gassing with argon and the suspension was stirred at room temperature for 1 hour. The reaction mixture was subsequently poured into 100 ml of water and extracted three times with 100 ml of petroleum ether each time. The organic phases were washed twice with 100 ml of water each time, dried over magnesium sulphate and concentrated. Low-pressure chromatography (0.5 bar) of the yellowish residue (1.16 g) on silver nitrate-coated silica gel with hexane/diethyl ether (vol. 90:10) gave 586 mg (48%) of p-[trans-4-(2E-pentenyl)cyclohexyl]-benzonitrile and 171 mg (14%) of p-[trans-4-(2Z-pentenyl)cyclohexyl]benzonitrile as colourless oils. The 2E-isomer has a melting point of 9.6° C. and 16.1° C. (2 modifications) and a virtual clearing point of −67° C.; the 2Z-isomer has a melting point of −7.7° C. and a virtual clearing point of −54° C.

The coating of silica gel of thin-layer plates with silver nitrate was carried out as follows;

34 g of silver nitrate were dissolved in 100 ml of acetonitrile. The thin-layer plates were dipped once for a short time in the silver nitrate solution and were thereafter dried for 2 hours at 80° C. in vacuo (12 Torr). 300 g of silica gel were then added to the remaining silver nitrate solution, mixed well, cautiously concentrated to dryness on a rotary evaporator and dried at room temperature in a high vacuum (0.5 Torr) for 2 hours.

EXAMPLE 3

(a) 10.0 g of 4'-bromo-4-phenylcarboxaldehyde and 5.31 g of copper(I) cyanide were dissolved in 80 ml of dimethylformamide while gassing with argon and the solution was heated to reflux for 15 hours at 180° C. bath temperature. Thereafter, the reaction mixture was poured cautiously into 200 ml of 25 percent ammonia and extracted three times with 200 ml of methylene chloride each time. The organic phases were washed once with 200 ml of 25 percent ammonia and twice with 200 ml of water each time, dried over magnesium sulphate and concentrated. Low-pressure chromatography (0.5 bar) of the yellowish, crystalline residue (8.7 g) on silica gel gave 5.85 g (74%) of 4'-cyano-4-biphenylcarboxaldehyde as slightly yellowish crystals; Rf-value (toluene/ethyl acetate vol. 90:10) 0.27.

(b) A suspension of 12.4 g of methoxymethyl-triphenylphosphonium chloride in 120 ml of t-butyl methyl ether was treated within 3 minutes with 4.1 g of potassium t-butylate while gassing with argon at 0° C. and the mixture was stirred for a further 1 hour at 0° C. Thereafter, the mixture was treated within 10 minutes with a solution of 5.0 g of 4'-cyano-4-biphenylcarboxaldehyde in 40 ml of tetrahydrofuran and the resulting mixture was stirred for a further 1.5 hours at room temperature. The reaction mixture was subsequently poured into 200 ml of water and extracted three times with 150 ml of diethyl ether each time. The organic phases were washed twice with 150 ml of water each time, dried over magnesium sulphate and concentrated. The residue obtained was dissolved in 25 ml of ethyl acetate and the solution was treated with 350 ml of petroleum ether. After leaving to stand for 10 minutes at −20° C. the precipitated triphenylphosphine oxide was filtered off and the filtrate was concentrated to dryness. Low-pressure chromatography (0.5 bar) of the dark brown oil (9.5 g) on silica gel with ethyl acetate/petroleum ether (vol. 10:90) gave 5.2 g (91%) of 4'-(2-methoxyvinyl)-4-biphenylcarbonitrile as yellowish crystals; Rf-value (ethyl acetate/petroleum ether vol. 10:90) 0.17.

(c) A mixture of 4.9 g of 4'-(2-methoxyvinyl)-4-biphenylcarbonitrile and 80 ml of glacial acetic acid/water (vol. 2:1) was heated to reflux for 1.5 hours at 100° C. bath temperature. The reaction mixture was subsequently poured into 150 ml of water and extracted three times with 100 ml of methylene chloride each time. The organic phases were washed with 100 ml of water and with 100 ml of saturated sodium hydrogen carbonate solution, dried over magnesium sulphate and concentrated. There were obtained 4.8 g of (4'-cyano-4-biphenylyl)acetaldehyde as a yellowish, crystalline residue which was processed without additional purification; Rf-value (toluene/ethyl acetate vol. 90:10) 0.37.

(d) (4'-Cyano-4-biphenylyl)acetaldehyde was converted in an analogous manner to paragraph (b) into 4'-(3-methoxy-2-propenyl)-4-biphenylcarbonitrile; Rf-value (ethyl acetate/petroleum ether vol. 10:90) 0.20.

(e) 4'-(3-Methoxy-2-propenyl)-4-biphenylcarbonitrile was converted in an analogous manner to paragraph (c) into 3-(4'-cyano-4-biphenylyl)propionaldehyde; Rf-value (toluene/ethyl acetate vol. 95:5) 0.34.

EXAMPLE 4

(a) 149 g of methoxymethyl-triphenylphosphonium chloride and 860 ml of t-butyl methyl ether were placed at room temperature in a sulphonation flask while stirring and gassing with nitrogen, the suspension was cooled to −10° C. and treated with 51.6 g of potassium t-butylate within 10 minutes. The suspension was stirred for a further 30 minutes at −10° C. to 0° C. and then treated dropwise within 45 minutes at 0° C. with a solution of 47.3 g of 4,4-ethylenedioxycyclohexanone in 720 ml of tetrahydrofuran. The orange suspension was stirred for a further 2 hours at room temperature, then poured into 5 l of hexane, stirred for 10 minutes and suction filtered. The filtrate was concentrated in vacuo and the yellow-brownish oil obtained (104.1 g) was treated with 500 ml of hexane and suction filtered. The filtrate was concentrated in vacuo, whereby 61.7 g of yellow-brownish oil were obtained. Chromatographic separation of this crude product on silica gel with methylene chloride/acetone (vol. 98:2 and 95:5) finally gave 53.5 g of 1,1-ethylenedioxy-4-(methoxymethylene)cyclohexane as a colourless oil.

(b) A mixture of 28.2 g of 1,1-ethylenedioxy-4-(methoxymethylene)cyclohexane, 770 ml of glacial acetic acid and 385 ml of water was heated to reflux for 1 hour in a round flask while gassing with nitrogen. Thereafter, the yellowish clear solution was cooled to room temperature, diluted with 800 ml of water and extracted three times with 700 ml of methylene chloride each time. The organic phases were washed twice with 500 ml of 10% (wt./vol.) sodium carbonate solution each time, dried over sodium sulphate, filtered and concentrated. Chromatographic separation of the brownish liquid obtained (18.5 g) on silica gel with methylene chloride as the eluent finally gave 16.7 g of 4-formylcyclohexanone as a brownish liquid.

(c) 63.3 g of p-cyanobenzyl-triphenylphosphonium chloride, 17.2 g of potassium t-butylate and 195 ml of ethylene glycol dimethyl ether were placed in a sulphonation flask while stirring and gassing with nitrogen, whereby the internal temperature rose to 44° C. The brown suspension was cooled to 0° C. and treated within 2 minutes with a solution of 16.7 g of 4-formylcyclohexanone in 100 ml of ethylene glycol dimethyl ether. Thereafter, the cooling bath was removed and the reaction mixture was stirred for a further 3.5 hours at room temperature. The suspension was subsequently poured into 500 ml of water and extracted three times with 600 ml of methylene chloride each time. The organic phases were washed twice with 500 ml of 10% (wt./vol.) sodium chloride solution each time, dried over sodium sulphate, filtered and concentrated, whereby 76.9 g of a brownish paste remained behind. Chromatographic separation of this crude product on silica gel with methylene chloride as the eluent gave 33.0 g of 4-[2-(p-cyanophenyl)vinyl]cyclohexanone as a yellow-brownish oil.

(d) A mixture of 33.0 g of 4-[2-(p-cyanophenyl)vinyl]cyclohexanone, 520 ml of toluene, 260 ml of ethanol and 3.2 g of palladium/carbon (5%) was placed at room temperature in a round flask equipped with a magnetic stirrer and the mixture was hydrogenated until the hydrogen uptake has come to a standstill. The black suspension was subsequently suction filtered (rinsing with toluene) and the filtrate was concentrated in vacuo. The slightly turbid, yellowish oil obtained (34.1 g) was separated by chromatography on silica gel. Methylene chloride/hexane (vol. 1:1), methylene chloride/hexane (vol. 8:2) and methylene chloride eluted 25.6 g of yellowish oil which was crystallized from t-butyl methyl ether. There were thus obtained 22.6 g of 4-[2-(p-cyanophenyl)ethyl]cyclohexanone as colourless crystals with m.p. 62.5°–64.3° C.

(e) A suspension of 54.4 g of methoxymethyl-triphenylphosphonium chloride in 315 ml of t-butyl methyl ether was treated with 18.8 g of potassium t- butylate while gassing with argon at −10° C. and the orange suspension was stirred for a further 30 minutes at 0° C. The mixture was subsequently treated dropwise within 30 minutes at 0° C. with a solution of 25.1 g of 4-[2-(p-cyanophenyl)ethyl]cyclohexanone in 260 ml of tetrahydrofuran and the mixture was stirred for a further 3 hours at room temperature. Thereafter, the reaction mixture was poured into 2.6 l of hexane, stirred for 10 minutes and suction filtered (rinsing with hexane). The filtrate was concentrated in vacuo at 50° C., whereby 47.7 g of yellow, partially crystalline residue were obtained. Low-pressure chromatography (0.3 bar) of the residue on silica gel with hexane/methylene chloride (vol. 4:1) and methylene chloride gave 21.0 g of p-[2-(4-methoxymethylenecyclohexyl)ethyl]benzonitrile as a yellowish oil; Rf-value (methylene chloride) 0.43.

(f) A mixture of 23.5 of p-[2-(4-methoxymethylenecyclohexyl)ethyl]benzonitrile and 300 ml of tetrahydrofuran/2N hydrochloric acid (vol. 4:1) was boiled at reflux while gassing with nitrogen for 30 minutes. The cooled reaction mixture was poured into 450 ml of water and extracted three times with 300 ml of diethyl ether each time. The organic phases were washed with 200 ml of water, dried over sodium sulphate and concentrated in vacuo at 50° C. There were obtained 21.9 g of 4-[2-(p-cyanophenyl)ethyl]cyclohexanecarboxaldehyde (trans/cis=4:1) as a colourless oil; Rf-value (methylene chloride) 0.3.

(g) A mixture of 21.9 g of 4-[2-(p-cyanophenyl)ethyl]cyclohexanecarboxaldehyde (trans/cis=4:1) and 167 ml of 0.1N methanolic potassium hydroxide solution was cooled to 0° C. while stirring and gassing with nitrogen, treated portionwise within 20 minutes with 3.5 g of sodium borohydride and thereafter stirred for a further 30 minutes at 0° C. Subsequently, the grey suspension was poured cautiously on to 420 ml of ice-water and extracted three times with 300 ml of methylene chloride each time. The organic phases were washed twice with 150 ml of water each time, dried over sodium sulphate and concentrated in vacuo at 50° C. The colourless, crystalline residue of p-[2-(4-hydroxymethylcyclohexyl)ethyl]benzonitrile (22.0 g, trans/cis=89.4:10.6) was dissolved in 100 ml of ethyl acetate while warming, treated with 100 ml of hexane and cooled to 15° C. while stirring, whereby crystallization occurred. The mixture was then treated with a further 300 ml of hexane while stirring, suction filtered (rinsing with hexane) and the precipitate was dried in vacuo at 50° C. The mother liquor was worked-up in an analogous manner and then the two crystallizates (a total of 17.3 g) were recrystallized from ethyl acetate/hexane. There were obtained 16.2 g (74%) of pure p-[2-(trans-4-hydroxymethylcyclohexyl)ethyl]benzonitrile as colourless crystals with m.p. 119.2°-121.1° C.

(h) A mixture of 9.3 g of oxalyl chloride and 166 ml of methylene chloride was treated dropwise within 10 minutes with a solution of 11.4 g of dimethyl sulphoxide in 33 ml of methylene chloride while stirring and gassing with nitrogen at −60° C. Thereafter, the mixture was treated dropwise within 15 minutes at −60° C. with a solution of 16.2 g of p-[2-(trans-4-hydroxymethylcyclohexyl)ethyl]benzonitrile in 66 ml of methylene chloride and the resulting mixture was stirred for a further 15 minutes at −60° C. Subsequently, the reaction mixture was treated dropwise within 15 minutes at −60° C. with 46.6 ml of triethylamine, the mixture was then warmed to room temperature within 30 minutes, poured into 330 ml of water and extracted three times with 200 ml of methylene chloride each time. The organic phases were washed twice with 200 ml of water each time, dried over sodium sulphate and concentrated at 50° C. in vacuo. Low-pressure chromatography (0.3 bar) of the resulting, brownish crystals (16.5 g) on silica gel with methylene chloride gave 14.4 g (89.6%) of pure trans-4-[2-(p-cyanophenyl)ethyl]cyclohexanecarboxaldehyde as colourless crystals with m.p. 90.0°-91.2° C.

(i) In an analogous manner to Example 1(c)–(i), trans-4-[2-(p-cyanophenyl)ethyl]cyclohexanecarboxaldehyde was converted into p-[2-(trans-4-(4-pentenyl)cyclohexyl)ethyl]benzonitrile; m.p. (C-I) 25.3° C., cl.p. (N-I) 17.2° C.

The following compound can be manufactured in an analogous manner:
p-[2-(trans-4-Allylcyclohexyl)ethyl]benzonitrile; m.p. (C-I) 39.7° C., cl.p. (N-I) −9.3° C.

EXAMPLE 5

A suspension of 3.16 g of ethyl-triphenylphosphonium bromide in 50 ml of dry t-butyl methyl ether was treated with 960 mg of potassium t-butylate while gassing with argon at −10° C. and the mixture was stirred for a further 45 minutes at 0° C. Thereafter, the mixture was cooled to −20° C., treated within 5 minutes with a solution of 1.45 g of 4-[trans-4-(p-cyanophenyl)cyclohexyl]butyraldehyde (purity 90%) in 20 ml of t-butyl methyl ether and the mixture was stirred for a further 30 minutes while warming to room temperature. The reaction mixture was subsequently poured into 100 ml of water and extracted three times with 100 ml of diethyl ether each time. The organic phases were washed with 100 ml of water, dried over magnesium sulphate and concentrated. Low-pressure chromatography (0.5 bar) of the residue on silica gel with ethyl acetate/petroleum ether (vol. 3:97) gave p-[trans-4-(4-hexenyl)cyclohexyl]benzonitrile (4Z:4E=88:12) as a colourless oil. Additional low-pressure chromatography (0.5 bar) of this material on 140 g of silver nitrate-coated silica gel (prepared according to Example 2) with hexane/diethyl ether (vol. 3:1) yielded 750 mg of p-[trans-4-(4Z-hexenyl)cyclohexyl]benzonitrile. Twofold recrystallization from methanol finally gave 468 mg of colourless crystals with m.p. (C-I) 27.4° C. and cl.p. (N-I) 4.5° C.

The following compound can be manufactured in an analogous manner:
4'-[trans-4-(2Z-Pentenyl)cyclohexyl]-4-biphenylcarbonitrile; m.p. (C-N) 81.9° C., cl.p. (N-I) 165.0° C.

EXAMPLE 6

(a) A mixture of 9.88 g of 4'-[trans-4-(4-pentenyl)cyclohexyl]-4-biphenylcarbonitrile, 735 ml of diethylene glycol and 79.9 g of potassium hydroxide was heated to 150°-160° C. while stirring and gassing with nitrogen and held at this temperature for 1 hour. Subsequently, the reaction mixture was cooled to room temperature and treated with 230 ml of semi-concentrated hydrochloric acid while cooling with an ice-bath. Thereafter, the reaction mixture was poured into 1.5 l of water, stirred at room temperature for 10 minutes and then suction filtered. The residue was washed neutral with water and dried in vacuo at 60° C., whereby 10.3 g (98.5%) of 4'-[trans-4-(4-pentenyl)cyclohexyl]-4-biphenylcarboxylic acid were obtained as colourless crystals.

(b) A mixture of 10.3 g of 4'-[trans-4-(4-pentenyl)cyclohexyl]-4-biphenylcarboxylic acid and 300 ml of acetone was cooled to 2° C. while stirring and gassing with nitrogen, treated dropwise within 10 minutes with a solution of 8.2 ml of triethylamine in 58 ml of acetone and stirred for a further 5 minutes. Thereafter, the mixture was treated dropwise at 0°-2° C. within 10 minutes with a solution of 7.1 ml of ethyl chloroformate in 29 ml of acetone. The mixture was stirred for a further 30 minutes at 0°-2° C. and treated dropwise within 10 minutes with a solution of 5.25 g of sodium azide in 29 ml of water. The reaction mixture was stirred for a further 2.25 hours while cooling with an ice-bath, then poured into 1 l of water and extracted once with 1 l of diethyl ether and once with 500 ml of diethyl ether. The ether phases were washed with water, dried over sodium sulphate, filtered and concentrated. The beige crystalline residue (12.2 g) was separated by chromatography on silica gel with methylene chloride, whereby 9.9 g (89.5%) of 4'(trans-4-(4-pentenyl)cyclohexyl]-4-biphenylcarboxylic acid azide were obtained as colourless crystals.

(c) A mixture of 9.9 g of 4'-[trans-4-(4-pentenyl)cyclohexyl]-4-biphenylcarboxylic acid azide and 215 ml of propanol was boiled at reflux while gassing with nitrogen for 30 minutes. Thereafter, the reaction mixture was concentrated, whereby 10.7 g (99.5%) of propyl 4'-[trans-4-(4-pentenyl)cyclohexyl]-4-biphenylcarbamate were obtained as colourless crystals.

(d) A mixture of 10.7 g of propyl 4'-[trans-4-(4-pentenyl)cyclohexyl]-4-biphenylcarbamate, 645 ml of diethylene glycol, 90.1 g of potassium hydroxide and 164 ml of water was heated for 17.5 hours in an oil bath of 170° C., then cooled to room temperature, poured into 800 ml of water and extracted three times with methylene chloride. The organic phases were washed twice with water, dried over sodium sulphate, filtered and concentrated. The brownish crystalline residue (8.2 g) was purified by chromatography on silica gel with methylene chloride/hexane (vol. 7:3), whereby 8.1 g (96%) of 4-amino-4'-[trans-4-(4-pentenyl)cyclohexyl]-4-biphenyl were obtained as beige crystals.

(e) A solution of 8.1 g of 4-amino-4'-[trans-4-(4-pentenyl)cyclohexyl]-4-biphenyl in 144 ml of chloroform was cooled to 4° C. while stirring and gassing with nitrogen and then treated with 7.14 ml of triethylamine. Subsequently, the mixture was treated dropwise at 0°-5° C. within 20 minutes with a solution of 2.33 ml of thiophosgene (purity 95%) in 71 ml of chloroform. The reaction mixture was stirred for a further 30 minutes at room temperature and then boiled at reflux for 1.5 hours. Subsequently, the reaction mixture was cooled to room temperature and washed with 110 ml of 3N ammonia solution and with 200 ml of water. The aqueous phases were back-extracted with methylene chloride. The organic phases were dried over sodium sulphate, filtered and concentrated. Two-fold chromatographic separation of the beige, crystalline residue (9.3 g) on silica gel firstly with hexane/methylene chloride (vol. 8:2) and then with hexane/chloroform (vol. 8:2) gave 8.2 g of a colourless, crystalline product. Recrystallization from acetone gave 6.788 g (74.1%) of 4'-[trans-4-(4-pentenyl)cyclohexyl]-4-biphenylyl isothiocyanate with m.p. (C-$S_B$) 95.5° C., $S_B$-$S_A$ 111.5° C., $S_A$-N 113.6° C., cl.p. (N-I) 213.5° C.

The following compounds can be manufactured in an analogous manner:

p-[trans-4-(4-Pentenyl)cyclohexyl]phenyl isothiocyanate; m.p. (C-I) 38.2° C., virtual cl.p. −10° C.,
p-[5-(4-pentenyl)-2-pyrimidinyl]phenylisothiocyanate; m.p. (c-$S_A$) 38.2° C., cl.p. ($S_A$-I) 62.5° C.

EXAMPLE 7

(a) A solution of methylmagnesium iodide in diethyl ether (prepared from 195 mg of magnesium shavings and 0.495 ml of methyl iodide in 15 ml of diethyl ether) was treated dropwise at room temperature with a solution of 1.0 g of p-[trans-4-(4-pentenyl)cyclohexyl]benzonitrile. The mixture was heated to reflux for 15 minutes. Subsequently, 15 ml of toluene were added to the reaction mixture, the diethyl ether was distilled off and the mixture was heated to reflux for a further 1.5 hours. Thereafter, the reaction mixture was treated cautiously at 0° C. with saturated ammonium chloride solution and partitioned three times in diethyl ether/water. The organic extracts were washed twice with water, dried over magnesium sulphate, filtered and evaporated. Chromatographic separation of the yellow crystalline residue (1.1 g) on silica gel with ethyl acetate/petroleum ether (vol. 5:95) gave 0.96 g (90%) of p-[trans-4-(4-pentenyl)cyclohexyl]acetophenone as light yellow crystals; m.p. 47.6° C.

(b) A solution of 0.9 g of p-[trans-4-(4-pentenyl)cyclohexyl]acetophenone in 8 ml of ethanol and 8 ml of diethylene glycol was treated with 350 ml of hydrazine hydrate while gassing with argon and the solution was then heated to reflux (bath temperature 110° C.) while stirring for 1 hour. Subsequently, the mixture was treated with 421 mg of solid potassium hydroxide, the bath temperature was increased to 210° C. and the ethanol was distilled off. After 3 hours at 210° C. the reaction was interrupted and the mixture was partitioned three times in water/petroleum ether. The organic extracts were washed twice with water, dried over magnesium sulphate and evaporated. Chromatographic separation of the residue (0.85 g) on silica gel with ethyl acetate/petroleum ether (vol. 3:97) gave 0.76 g (90%) of 4-ethyl-1-[trans-4-(4-pentenyl)cyclohexyl]benzene as a colourless oil; m.p. (C-I) −10.6° C.

The following compounds were manufactured in an analogous manner:

4'-Acetyl-4-[trans-4-(4-pentenyl)cyclohexyl]biphenyl; non-crystallizable at room temperature,
4'-ethyl-4-[trans-4-(4-pentenyl)cyclohexyl]biphenyl; cl.p. (S-I) 147.5° C., non-crystallizable to 0° C.,
4'-propionyl-4-[trans-4-(4-pentenyl)cyclohexyl]biphenyl,
4'-propyl-4-[trans-4-(4-pentenyl)cyclohexyl]biphenyl; cl.p. (S-I) 153.3° C., non-crystallizable to −50° C.,
p-[2-trans-4-allylcyclohexyl)ethyl]acetophenone; m.p. 33.9° C.,
4-ethyl-1-[2-(trans-4-allylcyclohexyl)ethyl]benzene; non-crystallizable to below −20° C., cl.p. −21° C., -[2-(trans-4-(4-pentenyl)cyclohexyl)ethyl]acetophenone; m.p. 32.4° C.
4-ethyl-1-[2-(trans-4-(4-pentenyl)cyclohexyl)ethyl]benzene; m.p. −16.9° C., cl.p. −5.1° C.

EXAMPLE 8

(a) A suspension of 11.5 g of 3,3-ethylenedioxypropyl-triphenylphosphonium bromide in 90 ml of t-butyl methyl ether was treated with 3.02 g of potassium t-butylate at 0° C. and the mixture was then stirred at room temperature for 40 minutes. Thereafter, the mixture was treated dropwise at 5° C. with a solution of 2.6 g of p-cyanobenzaldehyde in 30 ml of tetrahydrofuran and the resulting mixture was stirred for a further 1 hour at room temperature. The reaction mixture was subsequently treated with water. The phases were separated and the aqueous phase was back-extracted twice with methylene chloride. The organic phases were washed twice with water, dried over magnesium sulphate and concentrated. The residue was dissolved in hot ethyl acetate, the solution was treated with petroleum ether and the precipitated triphenylphosphine oxide was filtered off under suction. The yellow oil (4.5 g) obtained after concentrating the filtrate was purified by chromatography on silica gel with petroleum ether and petroleum ether/ethyl acetate. There were obtained 3.73 g (89.2%) of p-(4,4-ethylenedioxy-1-butenyl)benzonitrile as a light yellowish oil.

(b) A solution of 3.7 g of p-(4,4-ethylenedioxy-1-butenyl)benzonitrile in 50 ml of toluene was treated with 350 mg of palladium/carbon (5%) and the mixture was hydrogenated for 2.5 hours (hydrogen consumption 385 ml). The reaction mixture was then filtered (rinsing with diethyl ether) and the filtrate was evaporated. There were obtained 308 mg (82%) of p-(4,4-ethylenedioxybutyl)benzonitrile as a colourless, partially crystallizing oil.

(c) A mixture of 2.8 g of p-(4,4-ethylenedioxybutyl)benzonitrile, 56 ml of tetrahydrofuran and 56 ml of 10% hydrochloric acid was stirred for 3 hours at room temperature and then left to stand overnight. Thereafter, the reaction mixture was diluted with water and extracted three times with diethyl ether. The organic phases were washed twice with water, dried over magnesium sulphate, filtered and concentrated. There were obtained 2.6 g of 4-(p-cyanophenyl)butyraldehyde which was processed without additional purification.

(d) A suspension of 6.5 g of methyl-triphenylphosphonium bromide in 50 ml of t-butyl methyl ether was treated with 2.1 g of potassium t-butylate at −5° C. and the mixture was then stirred at room temperature for 40 minutes. Subsequently, the mixture was treated at 0° C. with a solution of 2.6 g of 4-(p-cyanophenyl)butyraldehyde in 30 ml of t-butyl methyl ether and the resulting mixture was stirred for 1 hour at room temperature. Thereafter, the reaction mixture was treated with water and extracted three times with diethyl ether. The organic phases were washed twice with water, dried over magnesium sulphate, filtered and concentrated. The crystalline residue was dissolved in hot ethyl acetate, the solution was treated with petroleum ether and the precipitated triphenylphosphine was filtered off. The oil obtained after concentrating the filtrate was purified by chromatography on silica gel with ethyl acetate/petroleum ether (vol. 5:95), whereby 1.92 g of p-(4-pentenyl)benzonitrile were isolated as a light yellowish liquid.

(e) A mixture of 1.9 g of p-(4-pentenyl)benzonitrile and a 10% solution of potassium hydroxide in diethylene glycol was boiled at 180° C. for 2 hours. The reaction mixture was then cooled to room temperature, adjusted to pH 3 with 23% hydrochloric acid, diluted with water and extracted four times with methylene chloride. The organic phases were washed twice with water, dried over magnesium sulphate, filtered and concentrated, whereby 2.12 g of p-(4-pentenyl)benzoic acid were isolated as brown crystals.

EXAMPLE 9

(a) A suspension of 829 mg of sodium borohydride in 20 ml of methanol/diethyl ether (vol. 9:1) was treated dropwise within 5 minutes at 0° C. with a solution of 3.0 g of trans-4-cyanocyclohexanecarboxaldehyde in 30 ml of methanol/diethyl ether (vol. 9:1). The reaction mixture was stirred for a further 2 hours at 10° C., then treated with 10 ml of dilute hydrochloric acid and partitioned in methylene chloride/water. The aqueous phase was extracted three times with methylene chloride. The organic phases were washed twice with water, dried over magnesium sulphate, filtered and concentrated. There were obtained 3.0 g (98%) of trans-4-(hydroxymethyl)cyclohexanecarbonitrile as a colourless oil.

(b) A solution of 3.0 g of trans-4-(hydroxymethyl)cyclohexanecarbonitrile in 10 ml of pyridine was treated dropwise within 3 minutes at 0° C. with a solution of 6.81 g of p-tosyl chloride in 10 ml of pyridine. The reaction mixture was stirred for 15 hours at room temperature, then made acid (pH about 2) with 50 ml of 25% hydrochloric acid and partitioned in chloroform/water. The aqueous phase was extracted three times with chloroform. The organic phases were washed twice with water, dried over magnesium sulphate, filtered and concentrated. There were obtained 6.3 g (99%) of trans-4-(p-tosyloxymethyl)cyclohexanecarbonitrile as colourless crystals.

(c) A solution of 6.3 g of trans-4-(p-tosyloxymethyl)cyclohexanecarbonitrile in 80 ml of acetone was treated with 3.87 g of sodium iodide and the mixture was heated to reflux while stirring for 15 hours. Thereafter, the white suspension was filtered and the filtrated was concentrated. The residue was partitioned in water/chloroform. The aqueous phase was extracted three times with chloroform. The organic phases were washed twice with water, dried over magnesium sulphate, filtered and concentrated. There were obtained 4.8 g (89%) of trans-4-(iodemethyl)cyclohexanecarbonitrile as a yellowish oil.

(d) A suspension of 9.14 g of copper(I) iodide in 90 ml of tetrahydrofuran was treated within 5 minutes at −78° C. with 25.7 ml of 1.5M solution of methyl lithium in tetrahydrofuran using a syringe. The suspension was stirred for a further 45 minutes at −78° C., then left to warm to 0° C. and stirred for a further 3 minutes at 0° C. Thereafter, the suspension was again cooled to −78° C. and treated within 5 minutes using a steel cannula with a Grignard solution prepared from 4.56 ml of 4-bromo-1-butene and 1.1 g of magnesium in 60 ml of tetrahydrofuran. The suspension was stirred for a further 20 minutes at −78° C., then left to warm to 15° C. and stirred for a further 5 minutes at 15° C. Thereafter, the solution was again cooled to −78° C. and treated dropwise within 5 minutes with a solution of 4.8 g of trans-4-(iodemethyl)cyclohexanecarbonitrile in 30 ml of tetrahydrofuran. Thereafter, the reaction mixture was left to warm and was stirred for a further 30 minutes at 16° C. Subsequently, the reaction mixture was treated cautiously in a cooling bath with about 50 ml of ammonium chloride solution and partitioned in methylene chloride/ammonium chloride solution. The aqueous phase was extracted three times with methylene chloride. The organic phases were washed once with ammonium chloride solution and twice with water, dried over magnesium sulphate, filtered and concentrated. Chromatographic separation of the yellow, oily residue (3.4 g) on silica gel with ethyl acetate/petroleum ether (vol. 5:95)

gave 2.9 g (85%) of trans-4-(pentenyl)cyclohexanecarbonitrile as a light yellow oil.

(e) A solution of 2.9 g of trans-4-(4-pentenyl)cyclohexanecarbonitrile in 80 ml of diethylene glycol was treated with 8.0 g of potassium hydroxide and the mixture was stirred for 3.5 hours at a bath temperature of 180° C. Subsequently, the reaction mixture was treated with ice, made acid with 25 ml of 25% hydrochloric acid and partitioned in methylene chloride/water. The aqueous phase was extracted three times with methylene chloride. The organic phases were washed twice with water, dried over magnesium sulphate, filtered and concentrated. Chromatographic separation of the brown, oily residue (3.5 g) on silica gel with ethyl acetate/petroleum ether (vol. 10:90) gave 2.9 g (90%) of trans-4-(4-pentenyl)cyclohexanecarboxylic acid as a yellowish oil.

EXAMPLE 10

(a) A solution of 400 mg of p-(3-hydroxypropyl)-phenol and 0.421 ml of triethylamine in 2.6 ml of methylene chloride was treated portionwise at 0° C. with 539 mg of p-tosyl chloride and the mixture was stirred for a further 5 minutes at 0° C. and for 15 minutes at −5° C. Subsequently, the reaction mixture was diluted with water, made slightly acid with dilute hydrochloric acid and extracted three times with methylene chloride. The organic phases were washed twice with water, dried over magnesium sulphate and freed from solvent. The residual, colourless oil (870 mg) was purified by chromatography on silica gel with ethyl acetate/petroleum ether, whereby 693 mg (83%) of p-(3-hydroxypropyl)-phenyl p-tosylate were isolated as a milky oil.

(b) A solution of 12 ml of oxalyl chloride in 380 ml of methylene chloride was treated dropwise at −60° C. with a solution of 19.8 ml of dimethyl sulphoxide in 30 ml of methylene chloride and the mixture was stirred for a further 5 minutes at −60° C. Subsequently, the mixture was treated dropwise with a solution of 38.9 g of p-(3-hydroxypropyl)phenyl p-tosylate in 100 ml of methylene chloride, the resulting mixture was stirred for a further 20 minutes at −60° C. and then treated with 88.5 ml of triethylamine. The reaction mixture was stirred for a further 5 minutes at −60° C., then left to warm slowly to room temperature and stirred for a further 5 minutes at 24° C. The reaction mixture was subsequently treated with water. The organic phases was washed with water and sodium chloride solution (back-extraction with methylene chloride), dried over sodium sulphate and evaporated. Chromatographic separation of the residual, brown-yellow oil (38 g) on silica gel with ethyl acetate/petroleum ether (vol. 40:60) gave 33.8 g of 3-[p-(p-tosyloxy)phenyl]propionaldehyde as a pale yellow oil.

(c) A suspension of 14.87 g of methoxymethyl-triphenylphosphonium chloride in 130 ml of t-butyl methyl ether was treated at −20° C. with 5.2 g of potassium t-butylate and the mixture was stirred without cooling for a further 1.2 hours. Subsequently, the mixture was treated dropwise at −5° C. with a solution of 8.8 g of 3-[p-(p-tosyloxy)phenyl]propionaldehyde in 30 ml of tetrahydrofuran. The cooling bath was removed and the mixture was stirred for a further 10 minutes at room temperature. The reaction mixture was then treated with water and partitioned twice in water/diethyl ether. The aqueous phases were back-extracted with diethyl ether. The organic phases were dried over magnesium sulphate and evaporated. The oily residue was dissolved in ethyl acetate and the solution was treated with petroleum ether and freed from precipitated triphenylphosphine oxide by filtration. After evaporation of the filtrate and chromatrographic separation of the residue on silica gel there were obtained 4.4 g (44%) of p-(4-methoxy-3-butenyl)phenyl p-tosylate as a slightly yellowish oil.

(d) A mixture of 4.3 g of p-(4-methoxy-3-butenyl)phenyl p-tosylate, 60 ml of glacial acetic acid and 30 ml of water was stirred for 40 minutes at 110° C., then cooled to room temperature and diluted with 200 ml of water. The aqueous phase was extracted four times with methylene chloride. The organic phases were washed twice with dilute sodium carbonate solution, dried over magnesium sulphate and freed from solvent. There were obtained 4.35 g of 4-[p-(p-tosyloxy)phenyl]butyraldehyde as a yellowish oil.

(e) A suspension of 7.32 g of methyltriphenylphosphonium bromide in 70 ml of t-butyl methyl ether was treated with 2.45 g of potassium t-butylate at −5° C. and the mixture was stirred for a further 40 minutes at room temperature. Subsequently, the mixture was treated slowly at 0° C. with a solution of 4.35 g of 4-[p-(p-tosylosy)phenyl]butyraldehyde in 30 ml of t-butyl methyl ether. The reaction mixture was stirred for a further 5 minutes at 0° C. and for 30 minutes at room temperature, then treated with water and partitioned twice in water/diethyl ether. The aqueous phases were back-extracted with diethyl ether. The organic phases were dried over magnesium sulphate and concentrated. The residue was dissolved in ethyl acetate and the solution was treated with petroleum ether and freed from precipitated triphenylphosphine oxide by filtration. After concentration of the filtrate and chromatographic separation of the residual, yellow oil (4.3 g) on silica gel there were obtained 3.37 g (78%) of p-(4-pentenyl)phenyl p-tosylate as a colourless oil.

(f) A mixture of 3.35 g of p-(4-pentenyl)phenyl p-tosylate and 50 ml of 10% ethanolic potassium hydroxide solution was stirred for 1 hour at 100° C. Subsequently, the reaction mixture was cooled to room temperature and made acid with dilute hydrochloric acid. The aqueous phase was extracted four times with diethyl ether. The organic phases were washed with water, dried over magnesium sulphate and concentrated. The residual brown oil (1.92 g) was purified by chromatography on silica gel with ethyl acetate/petroleum ether (vol. 8:92), whereby 1.70 g (99%) of p-(4-pentenyl)phenol were obtained as a light yellow oil.

EXAMPLE 11

A mixture of 520 mg of trans-4-(4-pentenyl)cyclohexanecarboxylic acid, 439.4 mg of p-ethoxyphenol, 765.5 mg of dicyclohexylcarbodiimide and 45 mg of 4-(dimethylamino)pyridine were dissolved in 80 ml of methylene chloride and the solution was stirred at room temperature for 20 hours. Subsequently, the reaction mixture was diluted with diethyl ether, the precipitated urea was filtered off and the filtrate was concentrated. The residue was taken up in hexane and the solution was washed with dilute hydrochloric acid, sodium hydrogen carbonate solution and water. The aqueous phases were back-extracted twice with hexane. The organic phases were dried over magnesium sulphate and evaporated. Low-pressure chromatography of the resulting residue on silica gel with ethyl acetate/petroleum ether (vol. 3:97) gave an 0.7 g (83%) of trans-4-(4-pentenyl)-cyclohexanecarboxylic acid p-ethoxyphenyl ester.

After recrystallization from 3 ml of methanol there were finally obtained 455 mg of product in the form of colourless crystals; m.p. (C-N) 32.7° C., cl.p. (N-I) 57.5° C.

The following compounds were manufactured in an analogous manner:

trans-4-(4-Pentenyl)cyclohexanecarboxylic acid p-propoxyphenyl ester; m.p. (C-N) 32.5° C., cl.p. (N-I) 43.5° C., trans-4-(4-pentenyl)cyclohexanecarboxylic acid 4-cyano-3-fluorophenyl ester; m.p. (C-I) 21.9° C., cl.p. (N-I) −26.9° C., trans-4-pentylcyclohexanecarboxylic acid p-(4-pentenyl)phenyl ester; m.p. (C-I) 33.3° C., cl.p. (N-I) 21.7° C., trans-4-(4-pentenyl)cyclohexanecarboxylic acid trans-4-butylcyclohexyl ester, p-pentylbenzoic acid p'-(4-pentenyl)phenyl ester; m.p. (C-N) 5.5° C., cl.p. (N-I) −7.6° C., p-(4-pentenyl)-benzoic acid p'-pentylphenyl ester; m.p. (C-N) 9.2° C., cl.p. (N-I) 14.0° C., p-(4-pentenyl)benzoic acid p'-cyanophenyl ester; m.p. (C-I) 38.4° C., p-(4-pentenyl)benzoic acid 4-cyano-3-fluorophenyl ester; non-crystallizable to −50° C., p-[trans-4-(4-pentenyl)cyclohexyl]benzoic acid p'-propylphenyl ester; m.p. (C-S) 73.1° C., S-S 88° C., S-N 109.5° C., cl.p. (N-I) 155° C.

EXAMPLE 12

(a) 7.05 g of sodium were dissolved in a solution of 40 g of diethyl malonate in 175 ml of ethanol. The still warm solution (50° C.) was treated dropwise within 15 minutes with 45.6 g of 5-bromo-1-pentene and the mixture was heated to boiling for 2 hours. After cooling the reaction mixture was poured into 500 ml of diethyl ether and 300 ml of semi-saturated sodium chloride solution. The aqueous phase was separated and back-extracted twice with 200 ml of diethyl ether each time. The organic phases were washed twice with 150 ml of semi-saturated sodium chloride solution each time dried over sodium sulphate, filtered and concentrated. Chromatographic separation of the resulting, yellow liquid (55.2 g) on silica gel with hexane/ethyl acetate (vol. 95:5) gave 33.2 g of diethyl (4-pentenyl)malonate as a colourless liquid.

(b) A suspension of 13.8 g of lithium aluminium hydride in 500 ml of tetrahydrofuran was treated dropwise under nitrogen at 0°–5° C. within 1 hour with a solution of 33.2 g of diethyl (4-pentenyl)malonate in 125 ml of tetrahydrofuran. The mixture was stirred overnight at room temperature and then heated to boiling for 3 hours. After cooling there were cautiously added dropwise to the reaction mixture firstly 25 ml of acetone and then 25 ml of saturated sodium hydrogen carbonate solution. The resulting slurry was suction filtered and the residue on the suction filter was washed four times with tetrahydrofuran. Concentration of the filtrate gave 17.8 g of 2-(4-pentenyl)-1,3-propanediol (purity 89%) as a yellow liquid.

(c) A mixture of 3.6 g of 2-(4-pentenyl)-1,3-propanediol, 4.4 g of p-butoxybenzaldehyde, 75 ml of toluene and 3 drops of 10% sulphuric acid was heated to boiling for 2.5 hours, whereby about 50 ml of wet solvent were distilled off and were replaced by the dropwise addition of 50 ml of fresh toluene. Thereafter, the mixture was neutralized with 4 drops of triethylamine and, after cooling, was extracted twice with 50 ml of 5% sodium hydrogen carbonate solution each time and twice with 50 ml of water each time. The organic phase was dried over sodium sulphate and concentrated. The residue (7.5 g) was chromatographed on silica gel with hexane/ethyl acetate (vol. 92:8), whereby 4.2 g of trans-4-(p-butoxyphenyl)-5-(4-pentenyl)-m-dioxane were obtained. Two-fold recrystallization from hexane gave 2.2 g of pure product with m.p. (C-N) 29.5° C. and cl.p. (N-I) 30.7° C.

The following compounds were manufactured in an analogous manner:

trans-2-(p-Ethoxyphenyl)-5-(4-pentenyl)-m-dioxane; m.p. (C-I) 35.6° C., cl.p. (N-I) 22.8° C., trans-2-(p-propoxyphenyl)-5-(4-pentenyl)-m-dioxane; m.p. (C-I) 36.2° C., cl.p. (S-I) 15.2° C., p-[trans-5-(4-pentenyl)-m-dioxan-2-yl]benzonitrile; m.p. (C-I) 38.0° C., cl.p. (N-I) 7.1° C.

EXAMPLE 13

(a) A suspension of 91.0 g of pyridinium chlorochromate in 650 ml of methylene chloride was treated dropwise within 5 minutes while stirring at room temperature with a solution of 22.6 g of 5-hexen-1-ol in 70 ml of diethyl ether and the mixture was stirred for a further 2 hours. Subsequently, the mixture was treated with 400 ml of diethyl ether and stirred for a further 15 minutes. Thereafter, the reaction solution was decanted off from a separated black resin and filtered. Fractional distillation of the filtrate under normal pressure gave, at 110°–122° C., 11.88 g of 5-hexenal.

(b) A suspension of 62.6 g of methoxymethyl-triphenylphosphonium chloride in 250 ml of diethyl ether was treated with 21.4 g of potassium t-butylate at 0° C. under nitrogen. The orange-red suspension obtained was treated dropwise within 15 minutes at 5°–10° C. with a solution of 11.88 g of 5-hexenal in 65 ml of diethyl ether and the mixture was stirred for a further 3 hours at room temperature. Thereafter, the reaction mixture was treated with 7.5 g of sodium hydrogen carbonate and 125 ml of water and stirred for 10 minutes. The aqueous phase was separated and back-extracted with 30 ml of diethyl ether. The organic phases were washed twice with 30 ml of water each time, dried over sodium sulphate and filtered. The filtrate was freed from solvent at 60° C. bath temperature under normal pressure. The distillation residue (a yellow liquid) was shaken with 400 ml of pentane until the undissolved residue had become solid. The suspension obtained was cooled to −25° C. and filtered. Fractional distillation of the filtrate under normal pressure gave, at 120°–143° C., 10.4 g of 1-methoxy-1,6-heptadiene.

(c) 13.2 ml of trimethyl orthoformate were treated with 0.22 ml of boron trifluoride diethyl etherate at 3° C. under an inert gas atmosphere. The mixture was then treated dropwise within 5 minutes while stirring with 2.52 g of 1-methoxy-1,6-heptadiene. The reaction mixture was left to stand in an ice-bath for a further 3 hours, then treated with 0.22 ml of triethanolamine and concentrated in a rotary evaporator at 50° C. The residue was dissolved in 30 ml of hexane and the solution was washed with 5 ml of saturated sodium hydrogen carbonate solution and four times with 5 ml of water each time, dried over sodium sulphate and concentrated. Bulb-tube distillation of the residue (4.0 g) at 220° C./9 Torr gave 3.74 g of (4-pentenyl)malonaldehyde tetramethyl acetal as a colourless liquid.

(d) A mixture of 3.74 g of (4-pentenyl)malonaldehyde tetramethyl acetal, 0.27 ml of water and 75 mg of p-toluenesulphonic acid monohydrate was heated for 2 hours at a bath temperature of 110° C. Thereafter, the mixture was treated with 0.12 ml of triethylamine, left to cool and poured into 80 ml of hexane. The reaction mixture was washed twice with 15 ml of saturated sodium hydrogen carbonate solution each time, dried over sodium sulphate and filtered. Concentration of the filtrate gave 2.4 g of crude 3-methoxy-2-(4-pentenyl)acrolein.

(e) A solution of 2.4 g of 3-methoxy-2-(4-pentenyl)acrolein and 3.4 g of p-pentylbenzamidine hydrochloride in 30 ml of methanol was treated dropwise while stirring with a sodium methylate solution prepared from 0.55 g of sodium and 5 ml of methanol. The reaction mixture was stirred overnight at 50° C. and then neutralized (pH 5) with 3N hydrochloric acid. The solvent was distilled off and the residue was taken up in diethyl ether and water. The aqueous phase was back-extracted with diethyl ether. The organic phase was phase was washed with water, dried over sodium sulphate and concentrated. Chromatographic separation of the residue on silica gel with hexane/ethyl acetate gave 5-(4-pentenyl)-2-(p-pentylphenyl)pyrimidine as a colourless liquid; m.p. (C-I) 8.0° C., cl.p. (N-I) −4.5° C.

The following compound is manufactured in an analogous manner:

5-(4-Pentenyl)-2-(p-ethoxyphenyl)pyrimidine.

We claim:

1. A compound of the formula

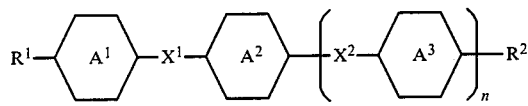

I wherein n is the integer 0 or 1; $X^1$ and $X^2$ are single covalent bonds or one of the $X^1$ and $X^2$ also is —COO—, —OOC— or —CH$_2$CH$_2$—; the rings $A^1$, $A^2$ and $A^3$ independently are 1,4-phenylene, 2-fluoro-1,4-phenylene or trans-1,4-cyclohexylene or one of these rings also is a 2,5-disubstituted pyrimidine or trans-2,5-disubstituted m-dioxane; $R^1$ is 4-alkenyl or when positioned on a cyclohexyl ring $R^1$ also can be 2Z-alkenyl; and $R^2$ is alkyl, alkoxy, —CN or —NCS; with the proviso that simultaneously $R^1$ is not 4-pentenyl, ring $A^1$ is not trans-1,4-cyclohexylene, $X^1$ is not —CH$_2$CH$_2$—, ring $A^2$ is not 1,4-phenylene, n is not the integer 0 and $R^2$ is not —CN.

2. The compound of claim 1 wherein the rings $A^1$, $A^2$ and $A^3$ independently are 1,4-phenylene or trans-1,4-cyclohexylene or one of these rings also can be 2,5-disubstituted pyrimidine or trans-2,5-disubstituted m-dioxane ring.

3. The compound of claim 2, wherein $X^1$ and $X^2$ are single covalent bonds or one of $X^1$ and $X^2$ also can be —COO— or —OOC—.

4. The compound of claim 2 wherein $R^1$ is a straight-chain 4-alkenyl of 5 to 12 carbon atoms or when positioned on a cyclohexyl ring $R^1$ also can be straight-chain 2Z-alkenyl of 3 to 12 carbon atoms.

5. The compound of claim 4, wherein $R^1$ is straight-chain 4-alkenyl of 5 to 12 carbon atoms.

6. The compound of claim 5, wherein $R^1$ is 4-pentenyl, 4Z-hexenyl or 4Z-heptenyl.

7. The compound of claim 2, wherein $R^2$ is straight-chain $C_1$-$C_{12}$-alkyl or when positioned on a benzene or pyrimidine ring $R^2$ also can be —CN, —NCS or straight-chain $C_1$-$C_{12}$-alkoxy.

8. A compound of the formula

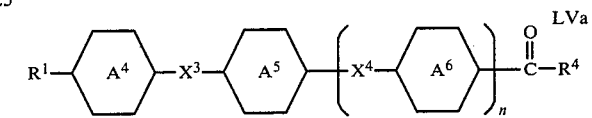

LVa wherein $X^3$ and $X^4$ are single covalent bonds or one of $X^3$ and $X^4$ also can be —CH$_2$CH$_2$—; rings $A^4$, $A^5$ and $A^6$ independently are 1,4-phenylene, 2-fluoro-1,4-phenylene or trans-1,4-cyclohexylene; $R^4$ is hydrogen or alkyl; n is the integer 0 or 1; and $R^1$ is 4-alkenyl or when positioned on a cyclohexyl ring $R^1$ also can be 2Z-alkenyl.

9. The compound of claim 1, wherein n is the integer 0, $X^1$ is a single convalent bond, ring $A^1$ is trans-1,4-cyclohexylene, ring $A^2$ is 1,4-phenylene, $R^1$ is 4-pentenyl and $R^2$ is ethyl, —CN or —NCS.

10. The compound of claim 1, wherein n is the integer 1, $X^1$ and $X^2$ are single covalent bonds, ring $A^1$ is trans-1,4-cyclohexylene, rings $A^2$ and $A^3$ are 1,4-phenylene, $R^1$ is 4-pentenyl and $R^2$ is ethyl, propyl, —CN or —NCS.

* * * * *